(12) United States Patent
Curry et al.

(10) Patent No.: US 9,079,181 B2
(45) Date of Patent: Jul. 14, 2015

(54) SAMPLE RECEIVING DEVICE

(75) Inventors: Ian Curry, Kanata (CA); Roy Sunstrum, Richmond (CA); Adele Jackson, Stittsville (CA); Rod Muir, South Mountain (CA); Romeo Graham, Chelsea (CA); Mike Sirois, Ottawa (CA)

(73) Assignee: DNA Genotek Inc., Kanata (CA)

( * ) Notice: Subject to any disclaimer, the term of this patent is extended or adjusted under 35 U.S.C. 154(b) by 19 days.

(21) Appl. No.: 12/737,821

(22) PCT Filed: Aug. 21, 2009

(86) PCT No.: PCT/CA2009/001153
§ 371 (c)(1),
(2), (4) Date: May 10, 2011

(87) PCT Pub. No.: WO2010/020043
PCT Pub. Date: Feb. 25, 2010

(65) Prior Publication Data
US 2011/0212002 A1     Sep. 1, 2011

Related U.S. Application Data

(60) Provisional application No. 61/090,822, filed on Aug. 21, 2008.

(51) Int. Cl.
  *G01N 33/00* (2006.01)
  *B01L 3/00* (2006.01)
  *B01L 9/00* (2006.01)

(52) U.S. Cl.
  CPC .......... *B01L 3/50825* (2013.01); *B01L 3/5029* (2013.01); *B01L 9/54* (2013.01);
(Continued)

(58) Field of Classification Search
  USPC .......................... 422/550, 547, 549, 561, 568
  See application file for complete search history.

(56) References Cited

U.S. PATENT DOCUMENTS

| 2,958,439 A | 11/1960 | Yochem |
| 3,419,179 A | 12/1968 | Deuschle et al. |

(Continued)

FOREIGN PATENT DOCUMENTS

| CA | 2 488 769 A1 | 12/2003 |
| CA | 2 488 769 A1 | 12/2003 |

(Continued)

OTHER PUBLICATIONS

International Search Report dated Nov. 27, 2009 for International Application No. PCT/CA2009/001153.
(Continued)

*Primary Examiner* — Sam P Siefke
(74) *Attorney, Agent, or Firm* — Mintz Levin Cohn Ferris Glovsky and Popeo, P.C.; David G. Conlin; Carolina E. Säve

(57) ABSTRACT

The present invention generally relates to a sample receiving device for releasably storing a substance. The sample receiving device includes a lid having a reservoir for retaining the substance, and a pierceable barrier sealing the substance within the reservoir; and b) a funnel for receiving a sample and configured for closure by the lid. The funnel is configured for releasable attachment to a sample receptacle such that a sample can be provided to the funnel and travel through the channel in the funnel into the sample receptacle. Further, the funnel includes one or more cutting ribs for cutting the pierceable barrier such that upon cutting of the pierceable barrier the substance is released from the reservoir, flows through the channel in the funnel and into the sample receptacle to be mixed with the sample. The present invention also provides a kit for collecting and storing biomolecules.

30 Claims, 36 Drawing Sheets

(52) U.S. Cl.
CPC .... *B01L2200/0689* (2013.01); *B01L 2200/085* (2013.01); *B01L 2200/141* (2013.01); *B01L 2200/16* (2013.01); *B01L 2200/185* (2013.01); *B01L 2300/021* (2013.01); *B01L 2300/043* (2013.01); *B01L 2300/044* (2013.01); *B01L 2300/047* (2013.01); *B01L 2300/0672* (2013.01)

(56) References Cited

U.S. PATENT DOCUMENTS

| | | |
|---|---|---|
| D213,292 S | 2/1969 | Arsenault |
| 3,799,426 A | 3/1974 | Pates et al. |
| D256,053 S | 7/1980 | Steigerwald |
| D287,570 S | 1/1987 | Olsen |
| 4,741,346 A | 5/1988 | Wong et al. |
| 4,753,358 A | 6/1988 | Virca et al. |
| D310,264 S | 8/1990 | Leoncavallo et al. |
| D318,727 S | 7/1991 | Spike |
| D325,444 S | 4/1992 | Murashita et al. |
| D355,606 S | 2/1995 | Manera |
| D357,985 S | 5/1995 | Burns |
| D362,184 S | 9/1995 | Carr |
| 5,567,309 A | 10/1996 | Classon et al. |
| D385,793 S | 11/1997 | Marsal |
| D424,440 S | 5/2000 | Wilkinson et al. |
| D425,625 S | 5/2000 | Niermann |
| D445,908 S | 7/2001 | Conway |
| D447,812 S | 9/2001 | Conway |
| D455,908 S | 4/2002 | Liu |
| 6,562,300 B2 | 5/2003 | Rosen et al. |
| 7,482,116 B2 | 1/2009 | Birnboim |
| 7,507,374 B2 * | 3/2009 | Gould et al. ................. 422/417 |
| D599,032 S | 8/2009 | Bucholtz et al. |
| D631,554 S | 1/2011 | Jackson et al. |
| D640,795 S | 6/2011 | Jackson et al. |
| 2004/0038269 A1 * | 2/2004 | Birnboim ........................ 435/6 |
| 2006/0210450 A1 | 9/2006 | O'Donovan |
| 2007/0009390 A1 | 1/2007 | Giusti |
| 2007/0272689 A1 | 11/2007 | Mitsuhashi |

FOREIGN PATENT DOCUMENTS

| | | |
|---|---|---|
| CA | 2 632 614 A1 | 6/2007 |
| CA | 2 632 614 A1 | 6/2007 |
| WO | 03/104251 A2 | 12/2003 |
| WO | 2006/096973 A1 | 9/2006 |
| WO | 2007/068094 A1 | 6/2007 |
| WO | WO-2007057744 A3 | 9/2007 |
| WO | 2008/040126 A1 | 4/2008 |

OTHER PUBLICATIONS

Search Notes for Design U.S. Appl. No. 29/368,375.
Dictionary entry for "Lid," p. 1615; The Compact Edition of the Oxford English Dictionary, vol. I, A-O; Oxford University Press 1971 (printed in the USA) (Twenty-second printing in US, Jun. 1982) (Oxford, New York, etc.).
OralStat Device; Quick Reference Guide; American Bio Medica Corporation 2008 (Kinderhook, New York); http://abmc.com/products/documents/QRG_OralStat.pdf.
European Search Report for Application No. 09807786.0 dated Oct. 22, 2012.
"Living hinge" from Wikipedia, the free encyclopedia (http://en.wikipedia.org/wiki/Living_hinge) (obtained Nov. 13, 2012).
Box With Living Hinge; efunda, Living Hinge; copyright 2012 (http://www.efunda.com/designstandards/plastic_design/hinge.cfm) (obtained Nov. 13, 2012).
Canadian Industrial Design Certificate of Registration, Registration No. 127470 dated Jun. 21, 2010.
Canadian Industrial Design Certificate of Registration, Registration No. 132896 dated Jun. 21, 2010.
Canadian Industrial Design Certificate of Registration, Registration No. 132897 dated Jun. 21, 2010.
European Community Design Application No. 001095186-0001 dated Feb. 20, 2009.
European Community Design Application No. 001095186-0002 dated Feb. 20, 2009.
European Community Design Application No. 001095186-0003 dated Feb. 20, 2009.
International Search Report for Application No. PCT/CA2009/001153 dated Nov. 27, 2009.
Search Notes for U.S. Appl. No. 29/368,375.

* cited by examiner

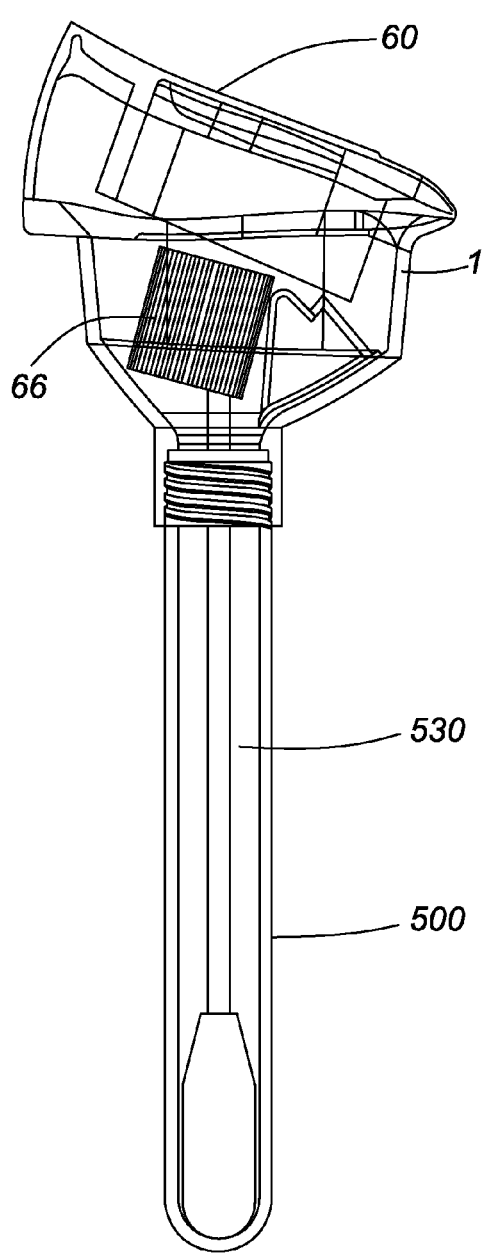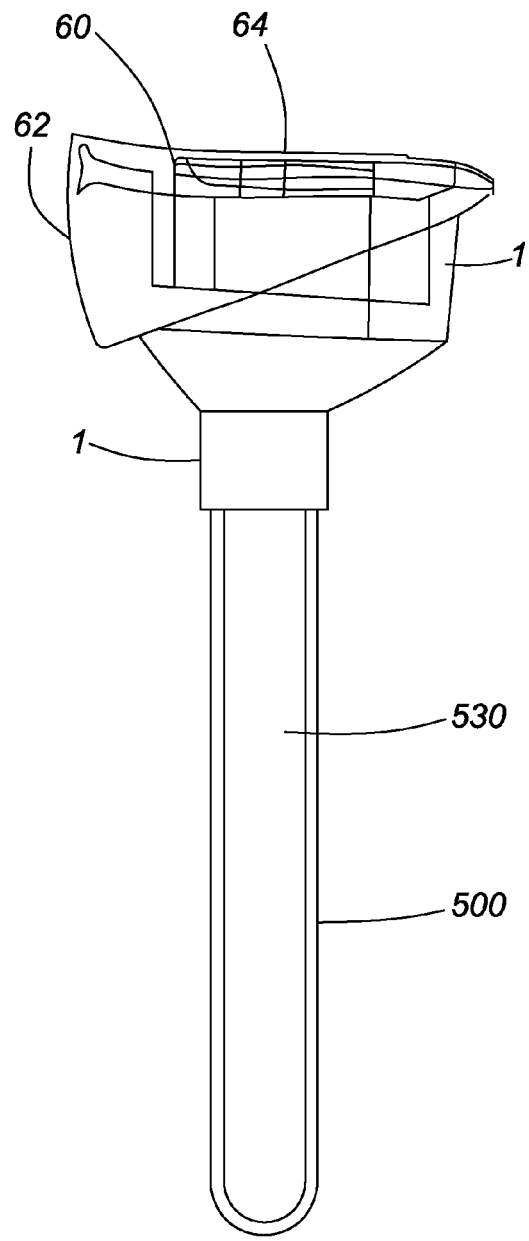
FIG. 6A  FIG. 6B

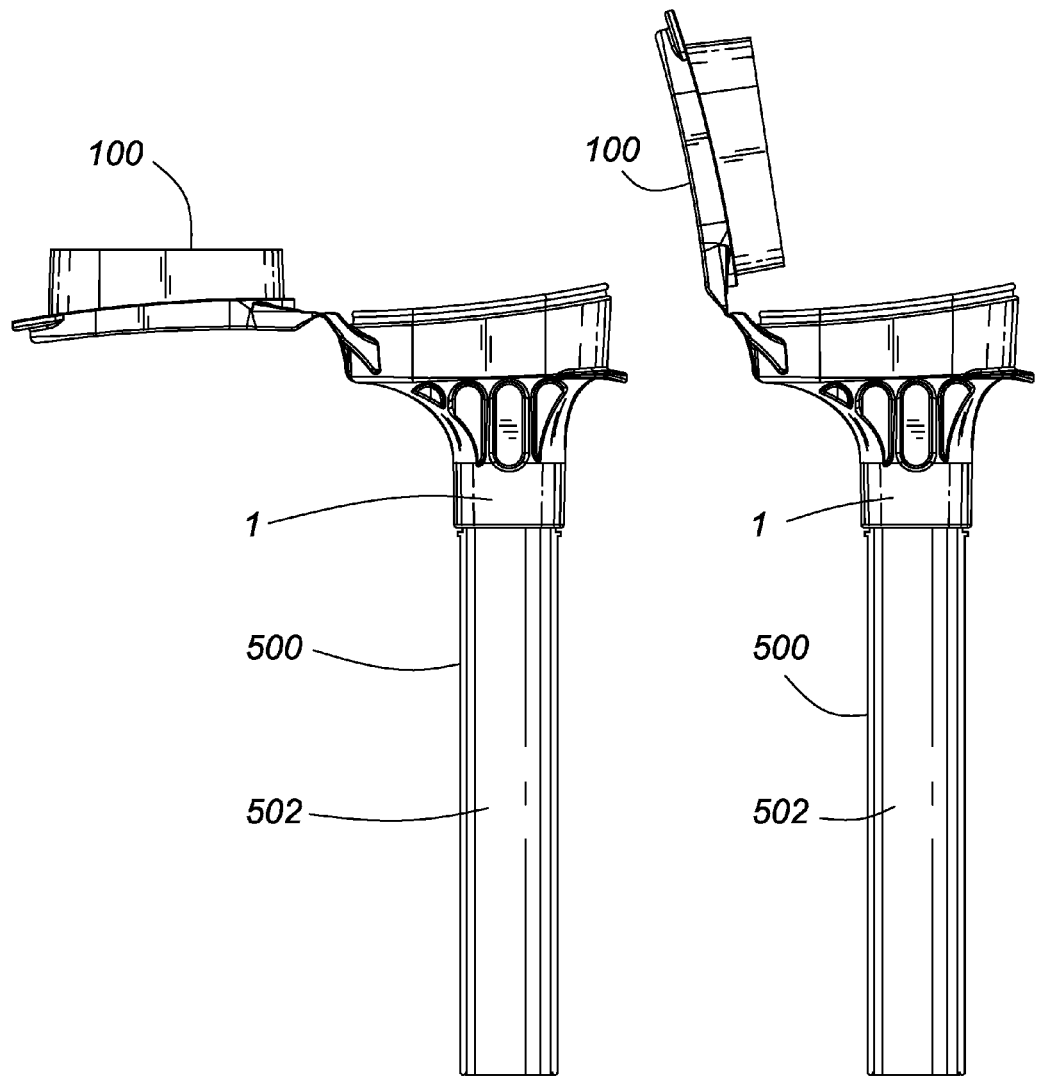
FIG. 12A    FIG. 12B

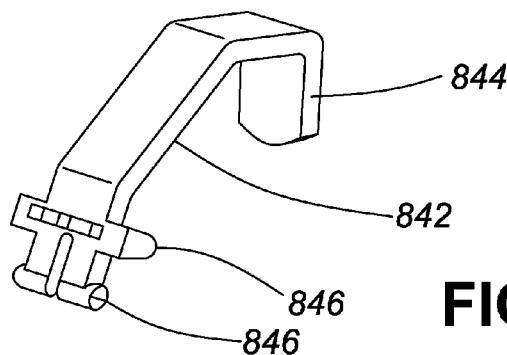
FIG. 26A
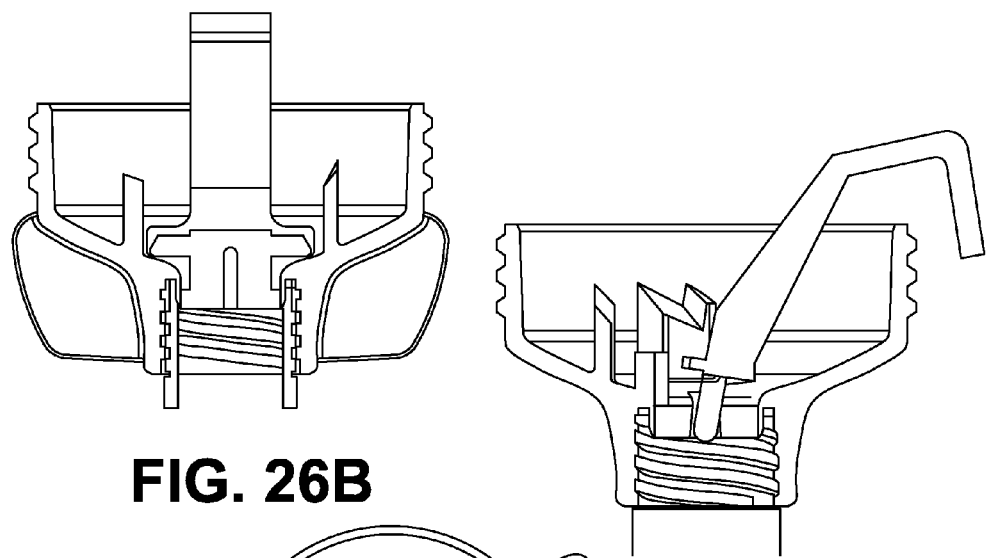
FIG. 26B   FIG. 26C
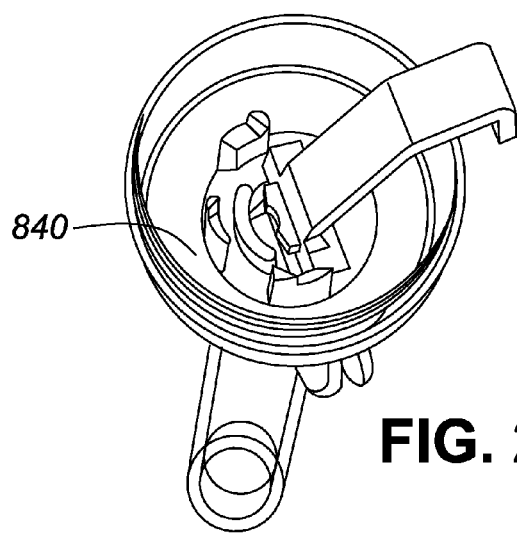
FIG. 26D

SAMPLE RECEIVING DEVICE

CROSS-REFERENCES TO RELATED APPLICATION APPLICATIONS

This application is the 35 U.S.C. §371 national stage of PCT application PCT/CA2009/001153, filed Aug. 21, 2009, which claims the benefit and priority to U.S. provisional patent application No. 61/090,822, filed Aug. 21, 2008, the disclosures of all of which are incorporated herein in their entirety as though set forth explicitly herein.

FIELD OF THE INVENTION

The field of the invention generally relates to a sample receiving device. More particularly, the invention relates to a sample receiving device that releasably stores a reagent.

BACKGROUND

It is often desirable to store a substance, such as a liquid, solid, gas or mixtures thereof, in a container prior to mixing with another substance(s). For example, it can be desirable to package and store a composition, or compositions, in a container for shipping and/or safe storage and handling, prior to combining with another material. A particular example is in the case of a toxic compound which needs to be stored securely within a container, prior to combining such a toxic compound with a detoxifying material. Another example is the case in which one or more concentrated active compositions need to be maintained separate from a diluent until immediately prior to use. Moreover, it can be desirable to store and/or ship diagnostic and/or biologic preserving compositions prior to combining such compositions with a biological sample. For example, it can be useful to keep one or more reagent compositions isolated from a donor until the donor's biological sample has been collected and deposited into a sample receiving device. This is particularly useful in preventing or minimizing accidental ingestion, contact or loss of the one or more reagent compositions during sample collection.

It can also be desirable to inactivate pathogens/infectious particles in a biological sample by combining it with a stored substance prior to storage and/or shipping and/or handling of the sample.

There are a variety of containers for holding substances separately in such a manner that a user may open a closure to combine the substances. Typically these containers are double compartment systems in which substances are stored separately and substances are combined by removal of the container closures by a user.

International PCT application WO 2003/104251 describes a container for collecting a biological sample from a subject, and subsequently mixing the collected sample with a composition intended to stabilize, preserve, or facilitate the recovery of components of the sample. This container has a first region for collecting a biological sample, a second region containing a composition for preserving a nucleic acid, and a barrier between the first region and the second region, which when in a closed position, maintains the sample and composition separate. The exemplified barrier of WO 2003/104251 is a pivoting partition. Attachment of a lid to the container forces the barrier to pivot from its original closed position spanning the container and thereby separating the first region and the second region, to an open position in which both regions are exposed to each other and contact between the composition contained in one region space and the biological sample contained in the other region is allowed. A drawback of this container is that it includes multiple parts (e.g., lid, vial, disk, rod, rod holder), which increases the cost of manufacture of the container. Additionally, because the disk is held in place by friction fit, there must be a high degree of precision for the manufacture of the components of the container. While the shape and size this container is well suited for collecting a biological sample from a donor, it does not lend itself well to high throughput analysis/testing or automation and is bulky/costly to transport.

International PCT Application No. PCT/CA2006/002009 describes a container system for releasably storing a substance. The container system includes a vial having a sample storage chamber and a piercing member for piercing a membrane in the lid, which membrane seals a substance within a reservoir in the lid until the membrane is pierced by the piercing member. The examples provided in this patent application disclose release of the substance as a result of twisting the lid during closing. The disclosed container system has two separate parts, requiring the user to properly align the lid and base before twisting on the lid.

Additionally, it may be desirable to use a sample receiving device that facilitates safe and effective sample collection by untrained and/or unsupervised donors. For example, where samples can be collected at home or remote locations where here is no access to medical personnel.

Typically, previous sample receiving devices relied on direct deposit of a sample in the device, or use of a sponge or absorbent tool/applicator which is deposited and held within the collection device together with the sample and storage solution (if present). Depending upon the nature of the substance released from the reservoir, the sponge may disintegrate and/or chemicals (e.g., adhesives) may be leached from the sponge and contaminate the sample. Importantly, the presence of the sponge/applicator in the sample may interfere with down-stream analysis, e.g., processing using liquid-handling robots. Liquid-handling robots may register an error upon contacting/colliding with a sponge in a sample; the robot may pierce through the sponge and successfully withdraw an aliquot, but inadvertently contaminate nearby samples as the pipette (with impaled sponge) passes over open tubes; there may be too little 'free' sample in the device for a robot or technician to recover for testing (i.e. the sponge soaks up and retains the sample-substance). In this case, extra handling is required to 1) manually remove the sponge(s) from the sample prior to storage and/or analysis, 2) manually recover sample retained within the sponge, and 3) pool 'recovered' sample with 'free' sample. It would be preferable to use a sample receiving device and a sample collection device without having to leave/deposit the applicator in the container.

There remains a need for an improved sample receiving device for releasably and reliably storing one or more substances.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

The present invention generally relates to a sample receiving device for releasably storing a substance.

In accordance with one aspect of the present invention, there is provided a sample receiving device for releasably storing a composition, comprising: (a) a lid comprising a reservoir for retaining said composition, and a pierceable barrier sealing said composition within said reservoir; and b) a funnel having a first open end for receiving a sample and a channel extending from said first open end to a second open end, said first open end configured for closure by said lid and said second open end being releasably or permanently attachable to a sample receptacle, wherein said funnel comprises one or more cutting ribs for cutting said pierceable barrier without a twisting action during closure of the lid.

In accordance with another aspect of the present invention, there is provided a sample receiving device for releasably storing a composition, comprising: a) a lid comprising a reservoir for holding a first substance, and a pierceable membrane sealing said first substance within said reservoir; b) a funnel having a first open end for receiving said sample and a channel extending from said first open end to a second open end, said first open end configured for closure by said lid and said second open end being releasably or permanently attachable to a sample receptacle, such as a vial or tube, wherein said funnel comprises (i) one or more cutting ribs for cutting said pierceable membrane without a twisting action during closure of the lid; and (ii) a tensioning means for maintaining tension on said pierceable membrane during cutting of said membrane.

In accordance with another aspect of the present invention, there is provided a sample receiving device for releasably storing a composition, comprising: a) a lid comprising a reservoir for holding a first substance, and a pierceable membrane sealing said first substance within said reservoir; b) a funnel having a first open end for receiving said sample and a channel extending from said first open end to a second open end, said first open end configured for closure by said lid and said second open end being releasably or permanently attachable to a sample receptacle, such as a vial or tube, wherein said funnel comprises (i) one or more piercing members for cutting said pierceable membrane without a twisting action during closure of the lid; and (ii) a tensioning means for maintaining tension on said pierceable membrane during cutting of said membrane; and (c) an expelling means for expelling the sample from a sample-containing absorbent device into the channel of said funnel.

In accordance with another aspect of the present invention there is provided a kit for releasably storing a substance comprising: a) a sample receiving device as described herein; and b) instructions for the use thereof. In the case where the sample receiving device does not include an integral sample receptacle, the kit would also include a sample receptacle for attachment to the second open end of the funnel. Typically, the kit also includes a cap for closing the sample receptacle following sample collection and removal of the funnel, and sponge(s) or tool/applicator(s) (if used). In addition, the kit can include a biohazard bag for safe transport (and containment) of the sample to it's destination (e.g. lab).

BRIEF DESCRIPTION OF THE FIGURES

FIG. 6A shows a shipping condition of a partially transparent side perspective views of the sample receiving device of FIG. 5, together with a lid guard;

FIG. 6B shows a closed condition of a partially transparent side perspective views of the sample receiving device of FIG. 5, together with a lid guard'

FIGS. 12A-12B depict a sample receiving device according to one embodiment of the present invention, in which the device is attached to a sample receptacle/tube. The device is shown with the lid in two different open positions.

FIGS. 26A-26D depicts an expelling clasp and its operative attachment to a sample receiving device to form an expelling mechanism in accordance with another embodiment of the present invention;

Figure 1A:
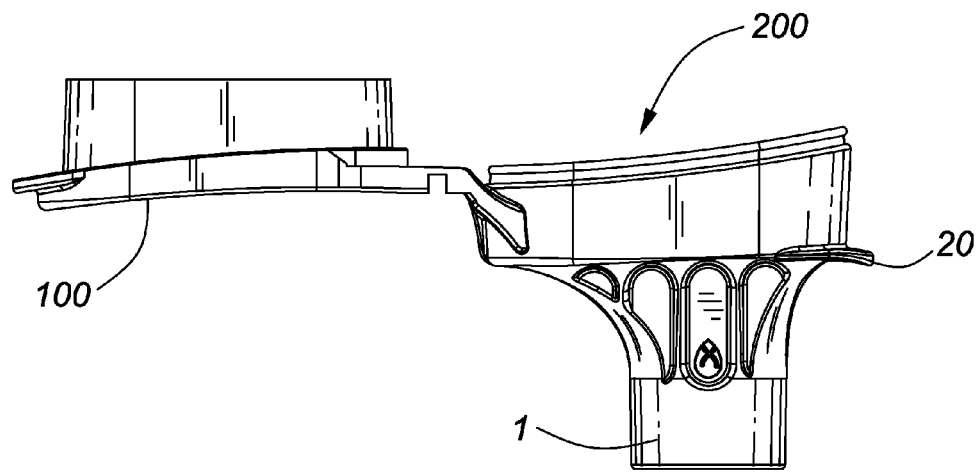
FIG. 1A is a side view and FIG. 1B cross section view of a sample receiving device in accordance with one embodiment of the present invention.

The numbers in bold face type serve to identify the component parts that are described and referred to in relation to the drawings depicting various embodiments of the present invention. It should be noted that in describing various embodiments of the present invention, the same reference numerals have been used to identify the same or similar elements. Moreover, for the sake of simplicity, parts have been omitted from some figures of the drawings.

DETAILED DESCRIPTION OF THE INVENTION

As will be discussed in more detail below, the present invention provides a sample receiving device designed to facilitate convenient sample collection and to maintain at least one substance, such as a preservative reagent, in a separate compartment for release into the sample following collection. The sample receiving device is further suitable for storing a concentrate/active ingredient separate from the substance stored in the lid, for example, as a dried mixture adhered to an inner surface of the lid, funnel and/or sample receptacle, such as a vial or tube, releasably or permanently attachable to the funnel.

The sample receiving device of the present invention has fewer component parts than are present in previously known sample receiving devices having a similar purpose. Thus, the device of the present invention can be less expensive and/or easier to manufacture and package, than such previous devices. Additionally, the manufacturing tolerances can be less precise for the sample receiving system of the present invention, as compared to previous systems having separate, releasable compartments (and threaded lids). Again, this reduces manufacturing cost, and makes accidental release of a sealed substance less likely. Depending on the specific embodiment employed, the device of the present invention can be manufactured with a low profile for ease of transport through the mail (for home collection); is typically easy to close since it requires less force than all or most of previously known devices and does not require a twisting action for closure and release of the substance(s) for mixing with the sample. In certain embodiments of the present invention, the user receives auditory feedback (e.g., a loud "snap") when the lid is fully closed. This is an advantage of the present device in comparison to those that require that a lid be twisted in order to facilitate a release of reagent, since the users of the previous device are often not certain when to stop twisting the lid for full closure as there is no obvious feedback. This previous design is readily cross-threaded, which can go unnoticed by the user resulting in sample leakage. Further, the lid can be designed for easy closure with the palm of hand for users with mobility/dexterity/gripping issues.

The sample collection device of the present invention comprises a funnel and a lid. The lid is configured to store a substance, and subsequently release the substance from the lid when the lid is sealingly attached to the funnel. In use, the substance stored within the lid is released through the funnel when the lid is used to close the sample receiving end of the funnel. The present invention further provides a sample collection (and recovery) system that comprises the device plus additional components. For example, and as described in further detail below, the system can additionally include a sample receptacle, such as a vial or tube, that is permanently or removably attached to the funnel. The system can also include a cap for closing the sample receptacle following sample collection and release of the stored substance(s) into the sample. The component parts of sample collection device and system of the present invention are described below with reference to the Figures.

Lid

Figure 1B:
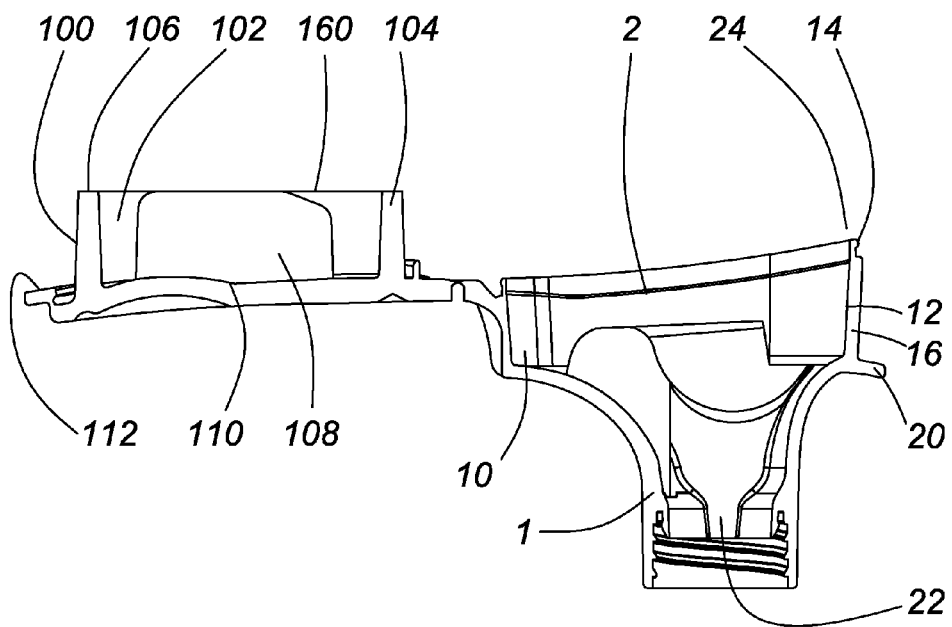
Figure 2:
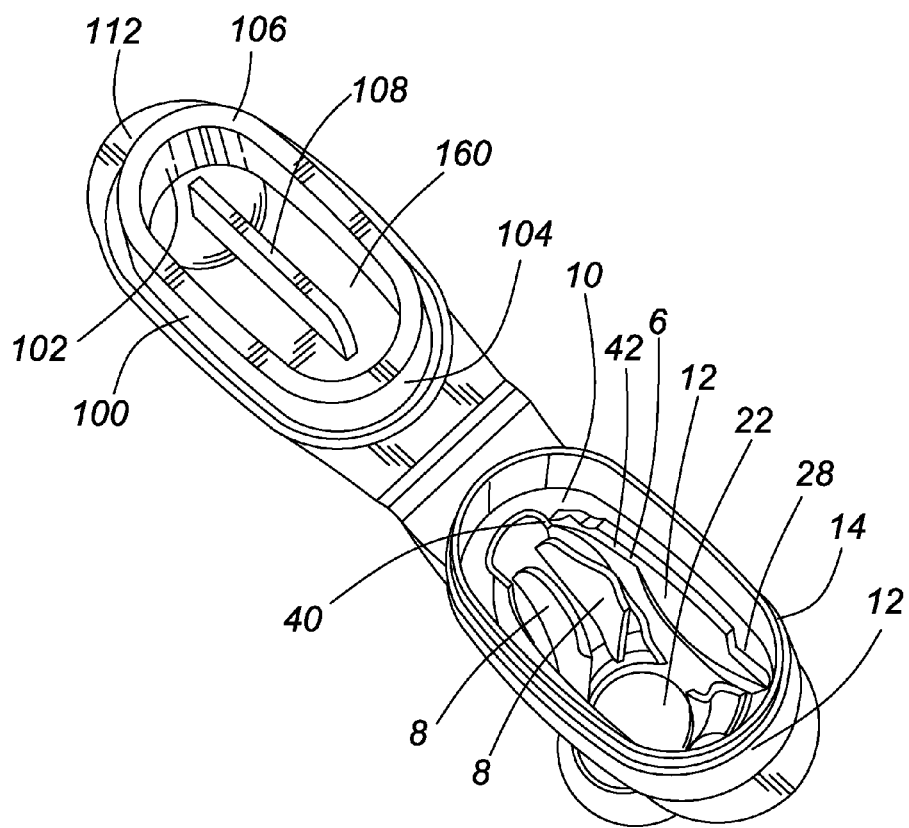
FIG. 2 is a top perspective view of the sample receiving device of FIGS. 1A-1B.

Referring to the figures, lid 100 releasably stores a substance within reservoir 102, which is sealed by pierceable membrane 160. The specific shape and dimensions of lid 100 are selected based on the application of the device. For example, as depicted in FIGS. 1A-1B and 2, lid 100 can be generally oval in shape and having a width selected to facilitate processing of the device in standard mail systems so that the user can ship the device with ease. However, the device of the present invention does not require that lid 100 be generally oval. Lid 100 can be a variety of shapes, as determined by the needs or preferences of the user and/or the intended application of use and/or shipping and packaging requirements.

Lid 100 includes wall 104 that defines reservoir 102 for holding a substance such as a liquid, solid, semi-solid, slurry, suspension, powder, colloid, gel, gas, mixtures thereof or the like. Wall 104 defines all or a portion of the perimeter of reservoir 102 and includes sealing surface 106 which is sealingly attached to pierceable membrane 160.

When attached to sealing surface 106, pierceable membrane 160 acts as a physical barrier to releasably store a substance within reservoir 102. Accordingly, pierceable membrane 160 is made from material that is inert to the substance to be stored within the reservoir and permits little or no diffusion or permeation of the substance through pierceable membrane 160 over time. Pierceable membrane 160 is made from a material that is suitable for the intended processing, storage and/or transportation conditions. Pierceable membrane 160 should be made from a material that remains non-reactive with the stored substance(s), the sample to be collected and any downstream processing reagents (if applicable). Similarly, the integrity of the membrane should remain unaffected by the conditions of intended use, packaging, transport and storage. Optionally, pierceable membrane 160 is chemical and/or temperature resistant. Pierceable membrane 160 can be made from a variety of materials including, but not limited to polymers such as polypropylene. Typically, the membrane is made from two or more layers of polymeric film. Desirably, the layer of pierceable membrane 160 that comes into direct contact with sealing surface 106 is made from the same material as wall 104. Optionally, the membrane is comprises foil, or thin sheets of aluminium, with the surface exposed to the substance, being coated, or being a layer made from, a material than remains non-reactive with the stored substance(s).

In a specific embodiment of the present invention, pierceable membrane 160 is heat and cold resistant such that it remains intact and pierceable at temperatures ranging from about −80° C. to about +130° C. or from about −20° C. to about +70° C.

In a specific embodiment of the present invention, pierceable membrane 160 is of sufficient strength and the seal between pierceable membrane and sealing surface 106 is sufficiently strong that the substance retained within reservoir 102 cannot be released by vacuum pressures.

The thickness of pierceable membrane 160 can vary according to application of use, and preference of the user. Desirably, pierceable membrane 160 has a thickness of about two thousandths of an inch. However, the specific thickness of the membrane will be determined by factors such as, nature of the substance, nature of the sample, overall dimensions of the container system, chemical composition of the membrane, tendency of membrane to puncture and propagate a tear, and transportation and storage conditions.

A variety of methods for attaching pierceable membrane 160 to sealing surface 106 can be used and are well known to workers skilled in the art. Selection of the appropriate manufacturing process is based on a number of factors, including the nature of the material used to make lid 100, the substance stored within reservoir 102, the conditions in which the device will be stored or shipped, and/or the characteristics of membrane 160. Selection of the appropriate method would be a matter of routine to a worker skilled in the art. Such methods of attachment include use of adhesive(s), heat-sealing treatment, fasteners, or any combination thereof, and the like. In a specific embodiment of the present invention, heat-sealing is used to attach pierceable membrane 160 to sealing surface 106. As will be clear to the skilled worker, the type of pierceable membrane, the physical and/or chemical properties of the pierceable membrane will be dependent upon, in part, the composition to be stored.

In one example, the perimeter of pierceable membrane 160 is generally flush with the outer perimeter of wall 104 when attached to sealing surface 106. In another example, the perimeter of pierceable membrane 160 overhangs the outer perimeter of wall 104 when attached to sealing surface 106. The absence, or extent, of an overhanging portion of pierceable membrane 160 is determined by the needs and/or preferences of the user and/or manufacturing tolerances.

In one example as depicted, for example, in FIGS. 1A, 1B, 2, 3B, 13-15, 33A-33B & 34A-34B, lid 100 includes an inner rib 108 which extends from inner surface 110 into reservoir 102. Inner rib 108 is positioned approximately centrally within reservoir 102 and one edge extending approximately parallel to the plane of pierceable membrane 160. This edge of inner rib 108 is preferably in close proximity to, and possibly abutting, the inner surface of pierceable membrane 160 but is not attached/sealed to pierceable membrane 160. Alternatively, this edge of inner rib 108 is sealed to pierceable membrane 160. It will be appreciated that rib 108 can be a variety of shapes and sizes, as determined by the needs and/or preferences of the user and/or manufacturing tolerances. In the examples depicted in the figures, rib 108 is approximately rectangular in shape. In use, rib 108 can assist in tensioning of pierceable membrane 160 during cutting and forms part of the tensioning means described in more detail below.

Lid 100 and reservoir 102 can be sized to accommodate a range of volumes of a substance. In the specific embodiment in which the substance is a reagent for preserving biological samples, such as nucleic acid containing saliva samples, reservoir 102 accommodates about 0.1 ml to about 10.0 ml of the preserving reagent. The lower amount of about 0.1 ml of preserving reagent is particularly suitable in the example in which the sample is cerebral spinal fluid, although it would also be useful for other sample types. With respect to the higher amount of about 10 ml of preserving reagent, this amount is particularly useful in the example when the sample is urine, although it would also be useful for other sample types. Typically, other sample types such as blood, saliva, etc. would require an intermediate amount of preserving reagent, for example, in the range of from about 0.2 ml to about 5.0 ml.

The choice of material used to manufacture lid 100 and/or rib 108 is dependent upon a number of factors including manufacturing constraints, chemical suitability, durability, aesthetics and the like. Lid 100 can be made from a variety of materials including polypropylene, medium-density polyethylene (MDPE), high-density polyethylene (HDPE), PVC, polycarbonate, and the like. In the specific embodiment in which the substance is a nucleic acid preservative for use with a saliva sample, lid 100 is made from plastics such us polypropylene, medium-density polyethylene (MDPE), high-density polyethylene (HDPE), polyethylene and the like. Desirably, lid 100 is polypropylene. The materials of lid 100 can be opaque, transparent or translucent, depending on the desired application. For example, an opaque material can be used to store a light sensitive composition(s) or sample. A transparent or translucent material is desirable if a visual (e.g., colour) indicator is present in the stored substance. Lid 100 and reservoir 102 can be manufactured to include gradations to demarcate the quantity of the substance stored within reservoir 102. The outer surface of lid 100 can also include a labelling area for a user to identify the contents of the reservoir. The outer surface of lid 100 may also include a region to affix or emboss a logo and/or other markings.

In accordance with one embodiment of the present invention, wall 104 defines a generally oval shape. However, it will be clear to the skilled worker that the shape and size of wall 104 is dependent upon the intended use(s) of the container system. Lid 100 may be constructed from a single piece of material that includes wall 104, or wall 104 may be removably attached to lid 100. Desirably, lid 100 is formed from a single piece of material. Irrespective of the manner by which wall 104 forms part of lid 100, it must be sized and shaped to permit use of lid 100 to close the open receiving end of funnel 1. In the Example depicted in for example, FIG. 3B, wall 104 is designed to nest within an exterior sloped wall about the open receiving end of funnel 1 when lid 100 is moved to close the open receiving end of funnel 1. Accordingly, the outer surface of wall 104 is sloped or tapered, and is configured to slidingly fit within the correspondingly sloped or tapered inner surface of the exterior wall of funnel 1. Optionally, there is essentially a zero draft on wall 104 and the exterior wall of funnel 1.

Figure 3A:
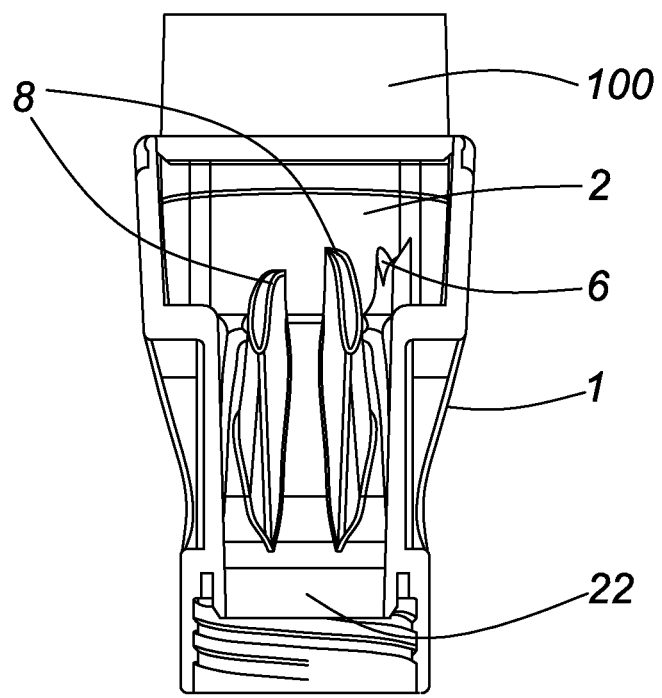
FIG. 3A is a partially transparent front view of the sample receiving device of FIGS. 1A-1B.
Figure 3B:
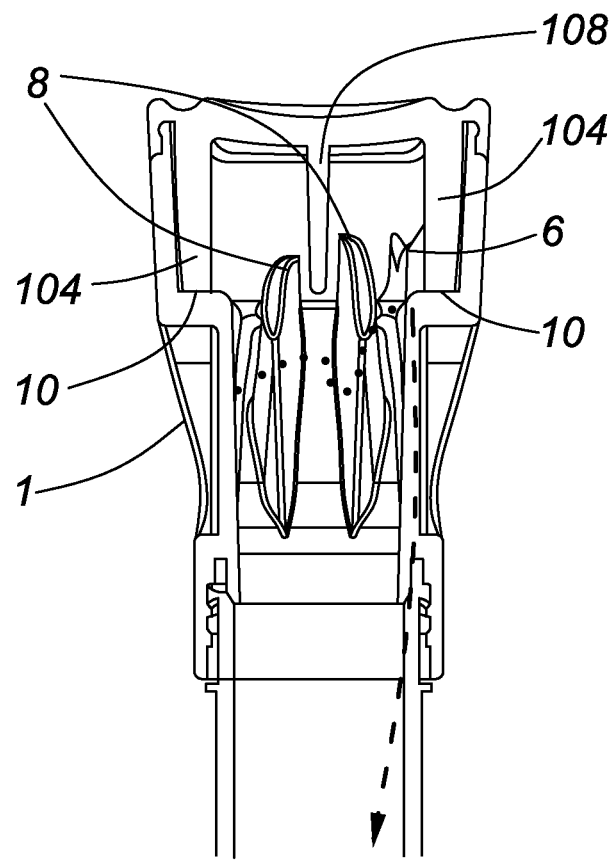
FIG. 3B is a partially transparent front view of the sample receiving device of FIG. 1, in which the dotted line depicts the ruptured membrane and the dashed line depicts the direction of fluid flow from the reservoir through the funnel channel.
Figure 3C:
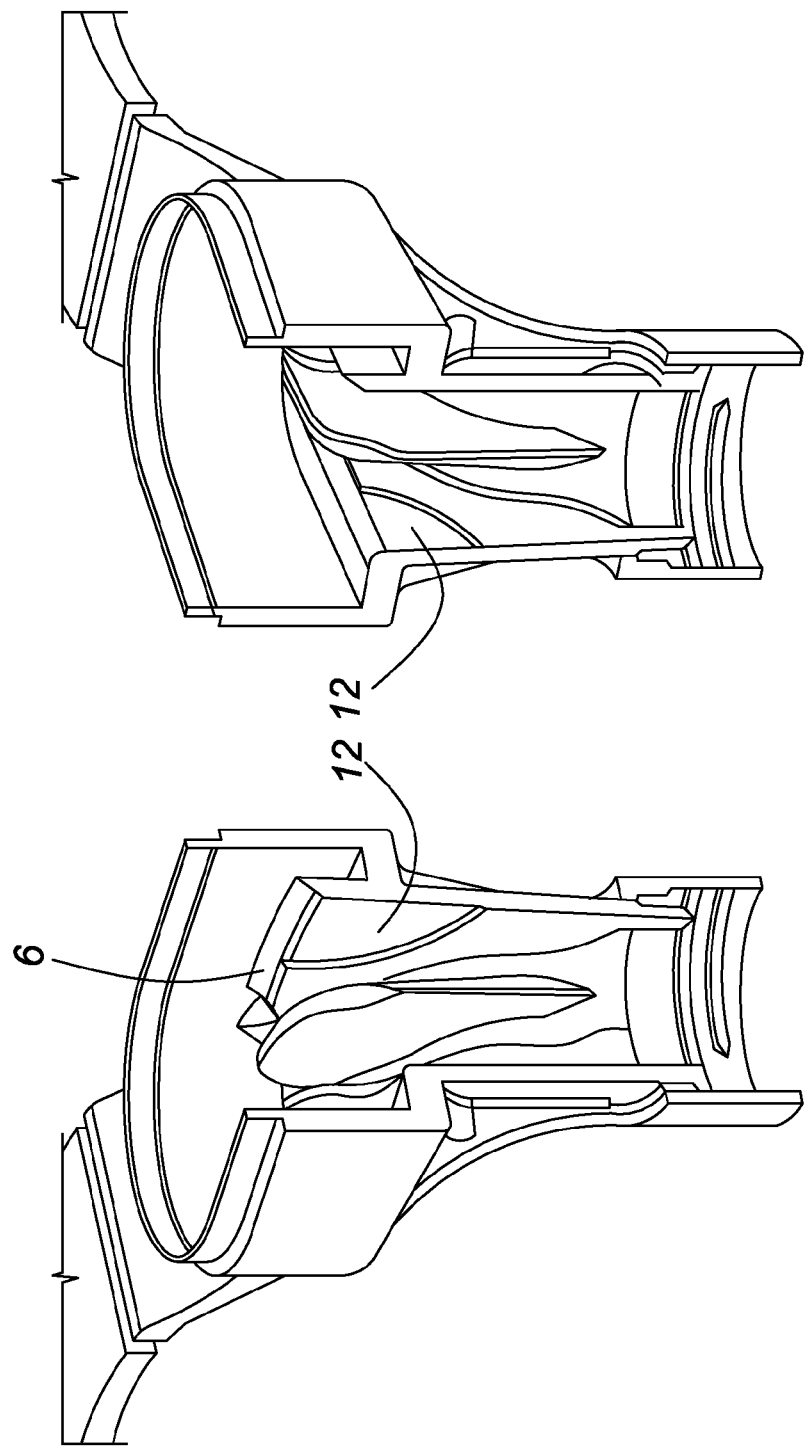
FIG. 3C shows partial perspective views of the sample receiving device of FIGS. 1A-1B.

In one embodiment of the present invention, as depicted in FIG. 3B, funnel 1 includes interior planar surface 10 adjacent to the interior wall. When lid 100 and funnel 1 are in a fully closed position such that wall 104 is nested within the exterior wall of funnel 1, sealing edge 106 of wall 104 engages interior planar surface 10 in funnel 1 in such a manner that a fluid-tight seal is formed. The presence of pierceable membrane 160 on sealing edge 106 can act as a gasket to further seal the interior of funnel 1 against leakage to the outside of the collection device. In a specific example, pierceable membrane 160 overhangs sealing edge 106. This overhanging membrane can also function as a gasket by occupying a portion of the region between wall 104 and the inner surface of the exterior wall of funnel 1, thereby preventing or minimizing leakage of the substance.

In an alternative embodiment of the present invention, funnel 1 does not include planar surface 10. Rather the surface is angled to facilitate a rapid evacuation of substance from the reservoir into the funnel and, subsequently, the sample receptacle. This feature is described in more detail below under the heading "Funnel".

In one embodiment of the present invention, lid 100 is configured for snap-fit with the open receiving end of funnel 1. In the specific example depicted in FIGS. 1A-1B and 2, lid 100 includes a closure skirt that extends about the periphery of wall 104 and includes inner depression 112 which is adapted to releasably engage circumferential ridge 14 about the upper edge of the open receiving end of funnel 1. Various alternative snap-seal or snap-fit configurations are well known to workers skilled in the art and can be used in the device of the present invention. In an alternate specific embodiment, the snap-fit closure is designed to provide audible and/or tactile feedback indicating when lid 100 has moved to a fully closed position and sealingly engaged funnel 1. In this fully closed position, pierceable membrane 160 will have been cut and the substance within reservoir 102 released into funnel 1. As such, this audible and/or tactile feedback also serves as an indication of release of the substance into funnel 1.

As would be appreciated by a skilled worker, alternative means for releasable attachment of lid 100 to funnel 1 can be used in the collecting device of the present invention, provided that lid 100 and funnel 1 are movable to a cutting position, as discussed in greater detail below, and provided that the releasable attachment ensures that the interior of funnel 1 is sealed against leakage to the outside of the collection device.

Figure 4A:
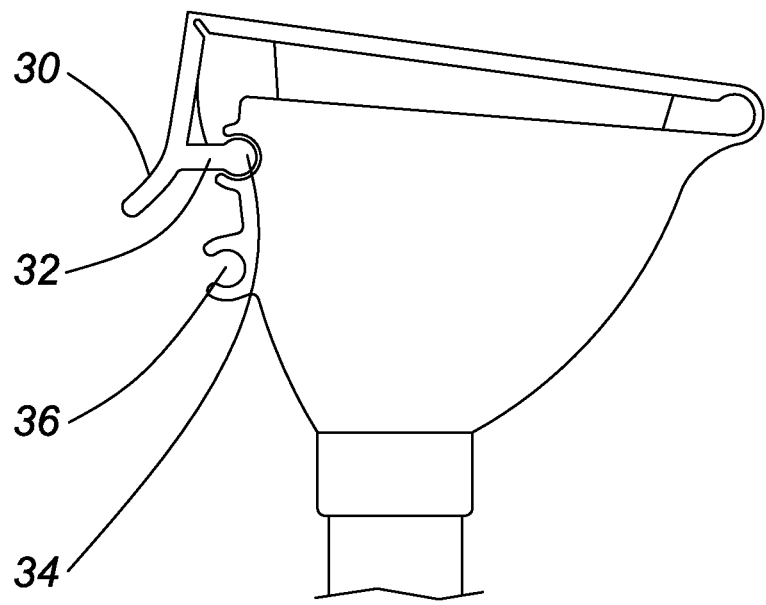
FIG. 4A shows a side view and FIG. 4B top perspective view depicting one embodiment of the sample receiving device of the present invention, in which the lid includes a locking tab that interacts with receiving notches in the funnel.

In an alternative embodiment, as depicted in FIG. 4A, lid 100 comprises tab 30 that includes locking arm 32 sized to be releaseably engaged by first receiving pocket 34 and second receiving pocket 36 on funnel 1. Optionally, the depicted in FIG. 4 also includes a partial snap seal (not shown). Tab 30 is movable from an open position to a first semi-closed position and from the first position to a locked position. In the first position, locking arm 32 of tab 30 is moved to and is releasably engaged by first receiving pocket 34 on funnel 1. In this first position, pierceable membrane 160 is not cut by the cutting rib(s) in funnel 1 and remains intact. When tab 30 is moved to the locked position, locking arm 32 is moved to and engaged by second receiving pocket 36. In this locked position, pierceable membrane 160 is cut by the cutting rib(s) in funnel 1 and the substance within reservoir 102 is released into funnel 1. In one example, the device includes a visual indicators to show a user whether locking portion 32 is in first receiving portion 34 or second receiving portion 36 and, consequently, whether or not the substance has been released from reservoir 102.

Figure 4B:
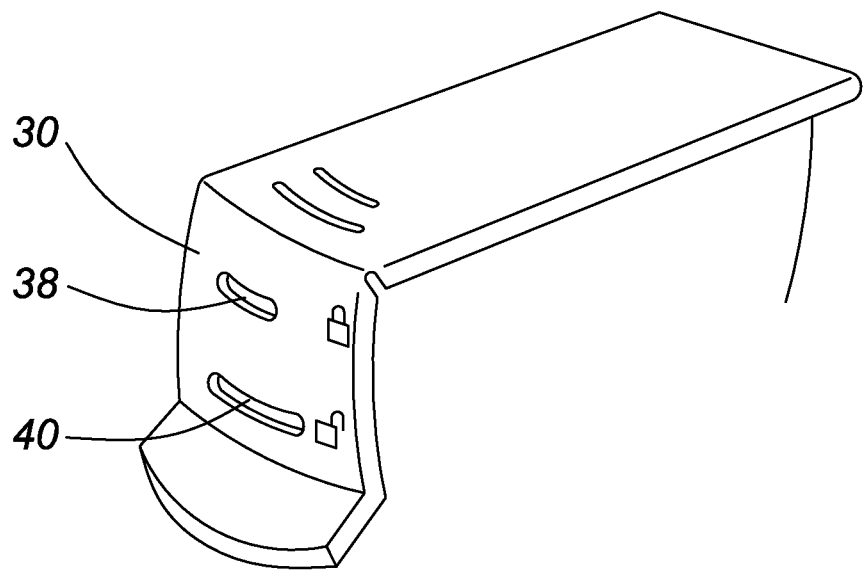
Figure 5:
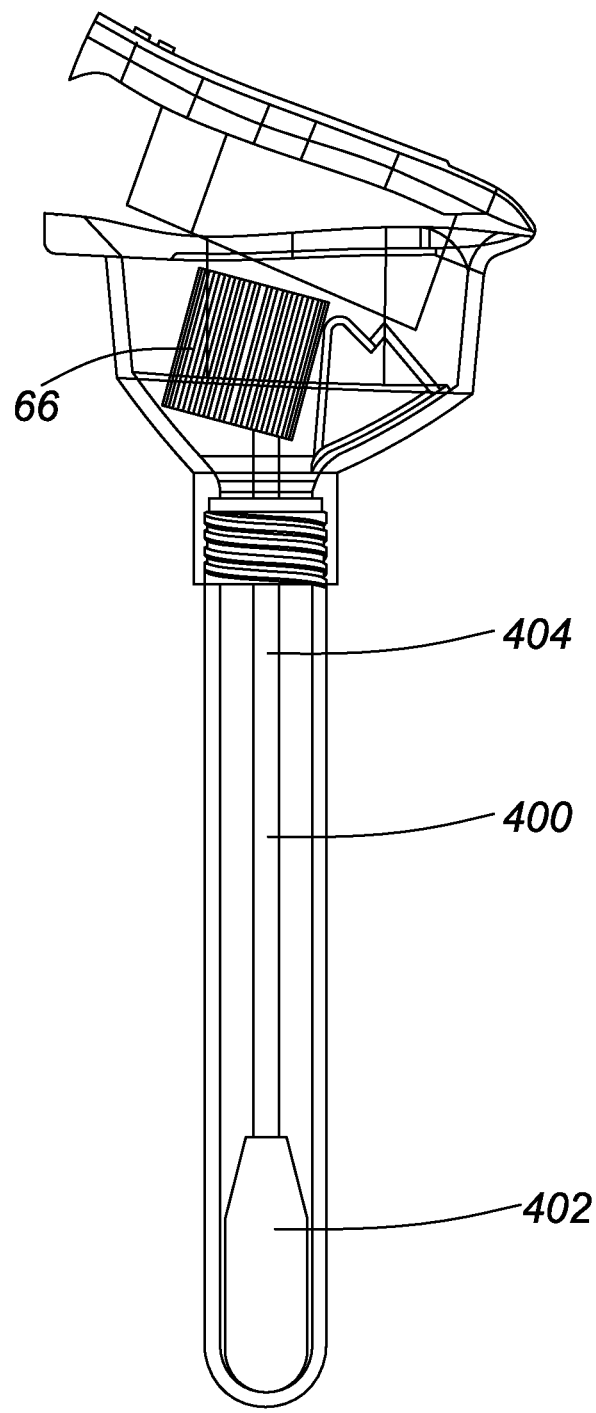
FIG. 5 is a partially transparent side perspective view of a sample receiving device in accordance with one embodiment of the present invention shown in shipping condition together with a cap and sample collection tool.
Figure 7:
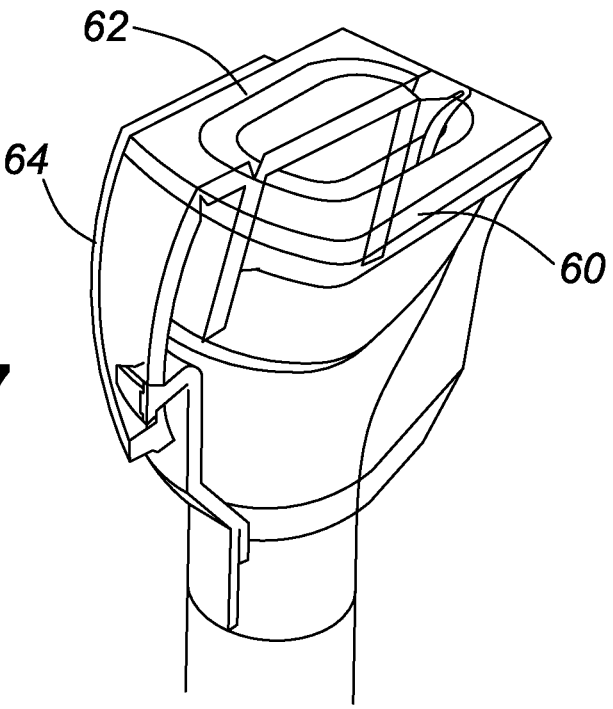
FIG. 7 depicts a partially transparent side view of a device of the present invention having a lid guard, in which the device is shown in a partially closed shipping position.
Figure 8:
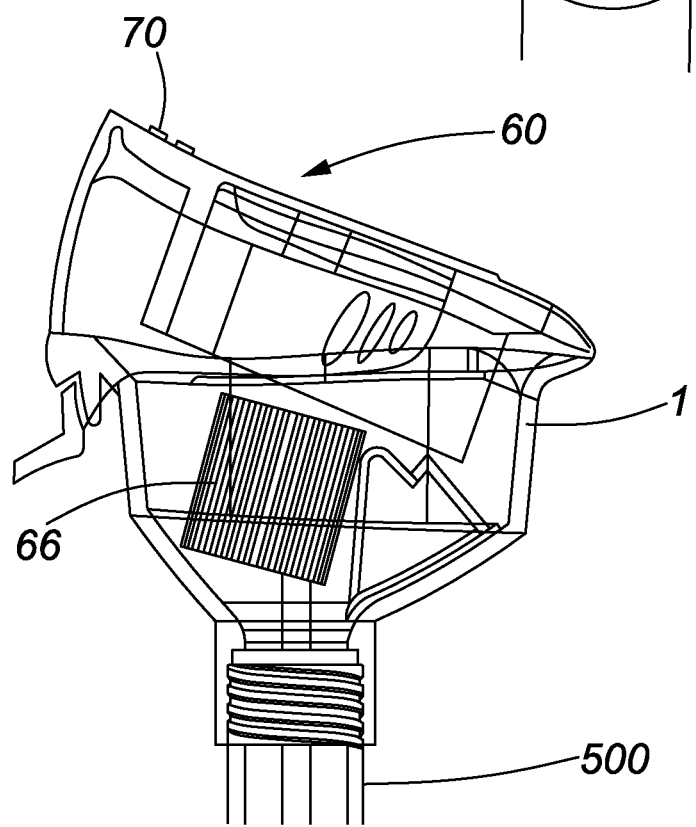
FIG. 8 is a partially transparent partial side view showing a lid guard on the sample receiving device of FIG. 5, in which the lid guard includes a tear-off strip.

In another example, as depicted in FIG. 4B tab 30 comprises a first receiving aperture 38 and second receiving aperture 40, and funnel 1 includes a protruding locking arm (not shown) adapted for releasable engagement by first receiving aperture 38 and second receiving aperture 40. As above, in this example, tab 30 is movable from an open position to a first position and to a locked position. In the first position, membrane 160 is not cut and remains intact. In the locked position, pierceable membrane 160 is cut and the substance is released from reservoir 102. In one example a visual indicator is used to show a user whether the locking arm 32 is in first receiving aperture 30 or second receiving aperture 40.

A worker skilled in the art will appreciate that alternative closure arrangements can be incorporated into the present system to ensure that the interior of funnel 1 is sealed against leakage to the outside. Such alternatives are considered to be within the scope of the present invention.

In the specific examples of FIGS. 1A-19 and 31A-34B, lid 100 and funnel 1 are connected by a living hinge. In an alternate example, lid 100 and funnel 1 are pivotally connected. It will be clear that lid 100 and funnel 1 can be attached in a variety of ways, for example, via tether strap or arm. In an alternate example, as shown in FIGS. 20-28, lid 100 and funnel 1 are separate elements of the device.

In the examples depicted in FIG. 6A-10, the sample collection system of the present invention further comprises lid guard 60. Lid guard 60 has closed top 62 and circumferential wall 64 depending therefrom, which wall is longest at the end of the lid opposite the hinge and tapers to join top 62 in the region adjacent the hinge of lid 100, and is configured for removable attachment to lid 100. Lid guard 60 includes means for removably retaining lid guard 60 on lid 100 and means for removable attachment to funnel 1 in such a manner that lid 100 is maintained in a partially closed position to ensure that pierceable membrane 160 is not ruptured prematurely. Lid guard 60 is configured to facilitate shipping and handling of the sample receiving device 200 and minimize the risk of inadvertent disruption of pierceable membrane 160 during, for example, shipping.

In one example, depending circumferential wall of lid guard 60 includes tear strip 65 and corresponding circumferential score line 70 intermediate to the retaining means, wherein when lid guard 60 is attached to lid 100 and funnel 1, a user can remove all or a portion of tear strip 65 so as to permit movement of lid 100 from the first position to the open position.

In another example, lid 100 is used in conjunction with a tamper detection/evident and/or tamper prevention seal, examples of which are shown in FIGS. 11A-11D. Such seals are well known to the skilled worker.

In accordance with a specific embodiment of the present invention, the lid is suitable to store a substance to stabilize, preserve or facilitate the recovery of nucleic acid from a biological sample. In accordance with a related embodiment, the funnel, or the combination of the funnel and vial is suitable for the collection of a biological sample from a subject.

Funnel

Funnel 1 of the sample receiving device of the present invention includes a first open receiving end for receiving a sample and a second open end for removable or fixed attachment to a sample receptacle, such as vial 500 as shown in FIGS. 12A-12B.

The term "sample receiving device" as used herein, does not include the sample receptacle unless it is fixedly attached or integral to the funnel. When the sample receptacle is not fixedly attached or integral to the funnel, the sample receptacle can form part of a sample receiving system that also includes the sample receiving device of the present invention. The sample receptacle can be removably attached to the second end of the funnel using standard means for attachment, for example, threaded engagement, snap-fit, etc. A description of such a removable sample receptacles is provided below. In the case in which the funnel includes an integral or fixed sample receptacle, the sample receptacle is considered to be a part of the sample receiving device. However, the characteristics of such an integral or fixed sample receptacle will be generally the same as the removable receptacle described below.

The interior of funnel 1 comprises interior channel 2 extending therethrough for receiving a sample, such as a liquid, solid, semi-solid, gas, slurry, suspension, colloidal suspension, gel, mixtures thereof and the like, and facilitating movement of the sample into vial 500. Interior channel 2 defines a region in fluid communication between the first open end and the second end generally referred to as flow path 22. Advantageously, the first open receiving end and interior channel 2 of funnel 1 are configured to facilitate collection of a biological sample, for example a sputum sample, such as saliva, and transfer of the sample into vial 500.

Funnel 1 can be a variety of shapes and sizes, as determined by the needs or preferences of the user and/or application of use and by size and shape of the lid (if preselected). In accordance with one embodiment of the present invention, open receiving end of funnel 1 is generally oval in shape. Alternatively, the first open end of funnel 1 is generally circular in shape. As depicted in FIG. 2, when the open receiving end of funnel 1 is oval, interior channel 2 is offset from the centre of the opening so as to provide a region for receiving the sample that corresponds to the opening of channel 2 and a second region having a bottom surface that slopes, or funnels, toward the opening of interior channel 2. The sloped surface about the opening of interior channel 2 acts to promote the flow of the sample and the substance ultimately released from reservoir 102 into the sample receptacle.

Although not necessary, it is typically preferable that the open receiving end of funnel 1 is generally wider than the second end of funnel 1. The generally wider open receiving end facilitates sample collection, by providing a (relatively) large opening. For example, the wide mouth or funnel characteristics can make it easier for a subject to deliver a sample into sample receiving device 200. In one example, as shown, for example, in FIGS. 1A-1B, 2 and 16A-18, the open receiving end of funnel 1 is oval shaped and the top edge is inclined to provide a raised portion 24 in the exterior wall of funnel 1. This raised portion 24 corresponds with the sample receiving region of funnel 1 and is configured to minimize sample loss as a result of the raised exterior wall.

Optionally, funnel 1 includes external tab 20 positioned at the base of funnel wall opposite from the hinged side of funnel 1. Tab 20 is designed for gripping by a user to support funnel 1 and/or funnel 1 and vial 500 during sample collection and/or during opening and closing of lid 100. For example, external tab 20 can be used by a user to assist in the closure of lid 100 (i.e., as leverage) by increasing the distance from the hinge/fulcrum at which force can be applied to close lid 100 on funnel 1

The choice of the material of funnel 1 and cutting rib(s) 6 is dependent upon a number of factors including manufacturing constraints, chemical suitability, ability to form a sharp point or knife edge, and the like. Some materials have better flow rates than others and will fill small spaces in the mould, like a knife edge. Materials with a poor flow rate in the same mould will produce a blunted knife edge. Additionally, the construction material of funnel 1 may be same or different as that used to make lid 100 and collection vial 500. In the specific embodiment in which the substance is a nucleic acid preservative for use with a saliva sample, funnel 1 is made from plastics such us polypropylene, high-density polyethylene (HDPE), polyethylene, medium-density polyethylene (MDPE), or any combination thereof, and the like. In one example, vial 500 is HDPE. In another example, vial 500 is polypropylene. In a specific example, lid 100 is polypropylene, vial 500 is polypropylene and funnel 1 is polypropylene.

Cutting Assembly

In accordance with the present invention, the funnel comprises a cutting assembly that includes one or more cutting ribs extending from an interior surface (e.g., sloped bottom surface) of funnel toward the open receiving end of the funnel. The cutting rib(s) is designed to pierce and cut the pierceable membrane during closure of the lid. The cutting assembly optionally includes tensioning means for maintaining tension on the pierceable membrane during cutting and for separating the cut portions of the membrane to avoid resealing. The cutting rib(s) and the tensioning means (if present) operate together to facilitate release of the substance from the reservoir in the lid during closing.

Figure 35A:
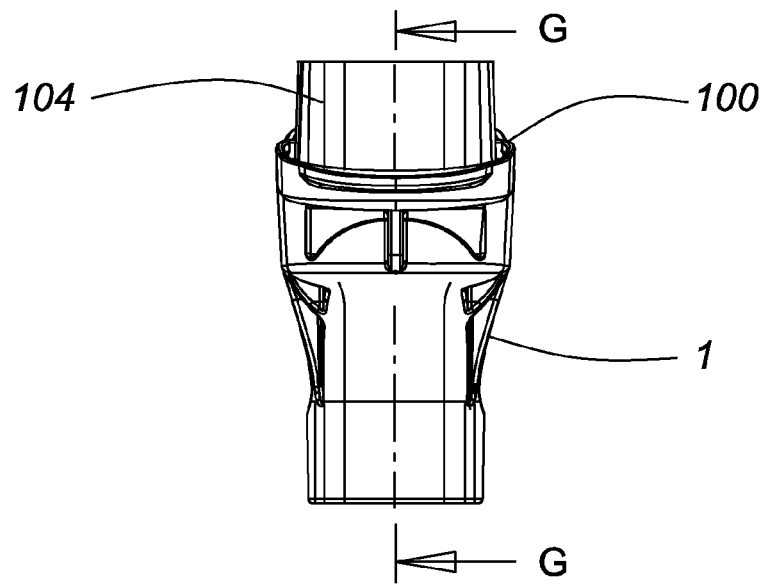
FIG. 35A depicts a front view and FIG. 35B is a cross-sectional view of the sample receiving device shown in FIGS. 34A-34B.
Figure 35B:
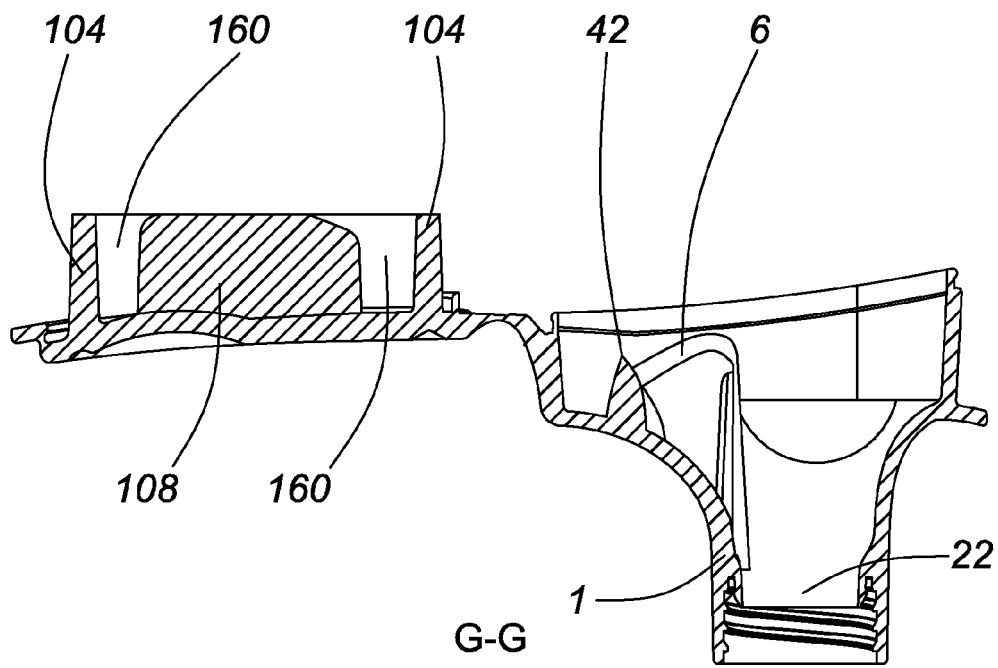

As shown in the figures, cutting rib 6 includes a sharp upper edge 7 designed to come into contact with and cut pierceable membrane 160 as lid 100 is moved into its closed position. The cutting assembly optionally includes one or more piercing tooth 42 that can be an integral part of the cutting rib, with or without an intermediate notch 41 separating piercing tooth 42 from cutting edge 7, or a separate upstanding element adjacent to cutting rib 6. Notch 41 if present, reduces the force required to pierce the pierceable membrane 160. However, pierceable membrane 160 will cut if notch 41 is absent, as in the cutting assembly depicted in FIGS. 35A-35B. Piercing tooth 42, when present, is the first part of the cutting assembly to contact and pierce pierceable membrane 160. Cutting edge 7 of cutting rib 6 acts to propagate the cut in pierceable membrane 160 from the hole/puncture made by piercing tooth 42. It will be appreciated that cutting rib 6 can be a variety of shapes depending on the needs and preferences of the user and/or manufacturer and/or nature of the pierceable membrane.

In accordance with one embodiment of the present invention, the sample collection device was designed to position the cutting elements apart from the sample receiving region of the funnel such that they in no way impede or interfere with the flow of the sample or substance into the sample receptacle. This off-set positioning also minimizes the possibility of user injury as a result of contact with the sharp components of the cutting assembly. In the embodiment of the invention depicted, for example, in FIG. 2, the sample receiving region provides a direct access to the sample receptacle via the interior channel of the funnel, which is important for 'low' volume samples, such as nasal samples, and for samples delivered through the use of a collection tool, such as a sponge. In the case where a collection tool is used, the user may need to trigger the kit to release the substance into the tube prior to depositing the sponge sample into the tube. The configuration in which the sample receiving region is off-set will provide a direct path to the substance (already released into the sample receptacle) via the interior channel, to wash the sample off the sponge. Once the sponge has been saturated with substance, the user can wring out the sample from the sponge with the squeegee tool (described in detail below) and then discard the sponge (instead of cutting or breaking the tip into the tube).

In accordance with one embodiment of the present invention, the cutting assembly comprises one cutting rib 6 (see, for example, FIG. 2). Alternatively, the cutting assembly comprises at least two cutting ribs 6 (see, for example, FIGS. 31A-31B), which can be arranged symmetrically on either side of the vertical plane extending through the length of oval shaped funnel 1 from the hinged end to the opposite end. Alternatively, the at least two cutting ribs are offset in relation to one another.

As depicted in FIGS. 1A-3C, cutting rib 6 and piercing tooth 42 can be positioned adjacent wall 16 such that it is removed from the center region of the open receiving end of funnel 1 and extends from between the opening of interior channel 2 and wall 16 to the region of funnel 1 having the sloping bottom surface. Alternatively, as depicted in FIGS. 32A-35B, cutting rib 6 and piercing tooth 42 are located more centrally and are spatially removed from the opening of interior channel 2. In this example, cutting rib 6 curves inward toward piercing tooth 42, which is positioned partially within or near the vertical plane extending through the length of oval shaped funnel 1 from the hinged end to the opposite end. Piercing tooth 42 is also positioned close to the hinged end such that it punctures pierceable membrane 160 at a point adjacent to reservoir wall 104.

The size and quality of the piercing and cutting of pierceable membrane 160 can degrade as the cut propagates due to the loss of tension in pierceable membrane 160. This loss of tension may result in incomplete cutting of pierceable membrane 160 and incomplete or slow release of the content of reservoir 102 into interior chamber 2 of funnel 1. The cutting rib(s) itself can block or slow the release of the substance if the tensioning system does not function to retract the opening and/or the membrane used is so compliant that it stretches considerably before rupturing. In accordance with one embodiment of the invention, the cutting assembly includes tensioning means to address this problem.

The tensioning means act to 1) maintain tension on the membrane enabling the cutting rib(s) to continue cutting the membrane over a longer distance; and 2) physically separate or spread apart the cut edges of the membrane and thereby prevent 'resealing' of the edges. This dual action helps to ensure rapid evacuation of the substance from the reservoir which, in turn, facilitates improved mixing of the substance with the sample (a quick flush as opposed to a slow trickle).

Depending upon the strength and type of pierceable membrane, a tensioning means may or may not be required. For instance, a very thin, brittle membrane that readily propagates a tear upon contacting a piercing member(s) can be sufficient to allow efficient release of the first substance. In deciding whether or not to include a tensioning means, the resilience (and toughness) of the membrane is considered in view of the need for robustness or durability during transportation and storage. Generally, the thicker, more compliant membranes are selected for their toughness and ability to withstand transport by air. However, this type of membrane does not readily propagate a tear and may 'self-seal' with itself when the piercing member is used alone, which significantly hinders efficient release of the substance.

The tensioning means can include lid inner rib 108 described above and one or more pusher ribs. During the cutting process lid inner rib 108 engages pierceable membrane 160, urging it away from the site(s) of disruption, thereby maintaining a suitable tension in pierceable membrane 160 for continued disruption of pierceable membrane 160. The tensioning means further comprises one or more tension ribs that act to engage pierceable membrane to maintain tension throughout the cutting process. The tension rib(s) projects upward from the sloped bottom surface of the funnel and have a blunt or curved upper edge. In one embodiment of the invention, the tension rib(s) is a rigid upstanding element. However, in an alternative embodiment of the invention, the tension rib(s) is a resilient or flexible element that will bend during tensioning as result of the cutting process. The resilient tension rib(s) can exhibit the features of a linear spring, which can improve the tensioning provided by the tension rib(s) as compared to that provided by a rigid tension rib. Again, selection of the appropriate alternative is, at least in part, based on the film characteristics of the pierceable membrane.

Figure 18:
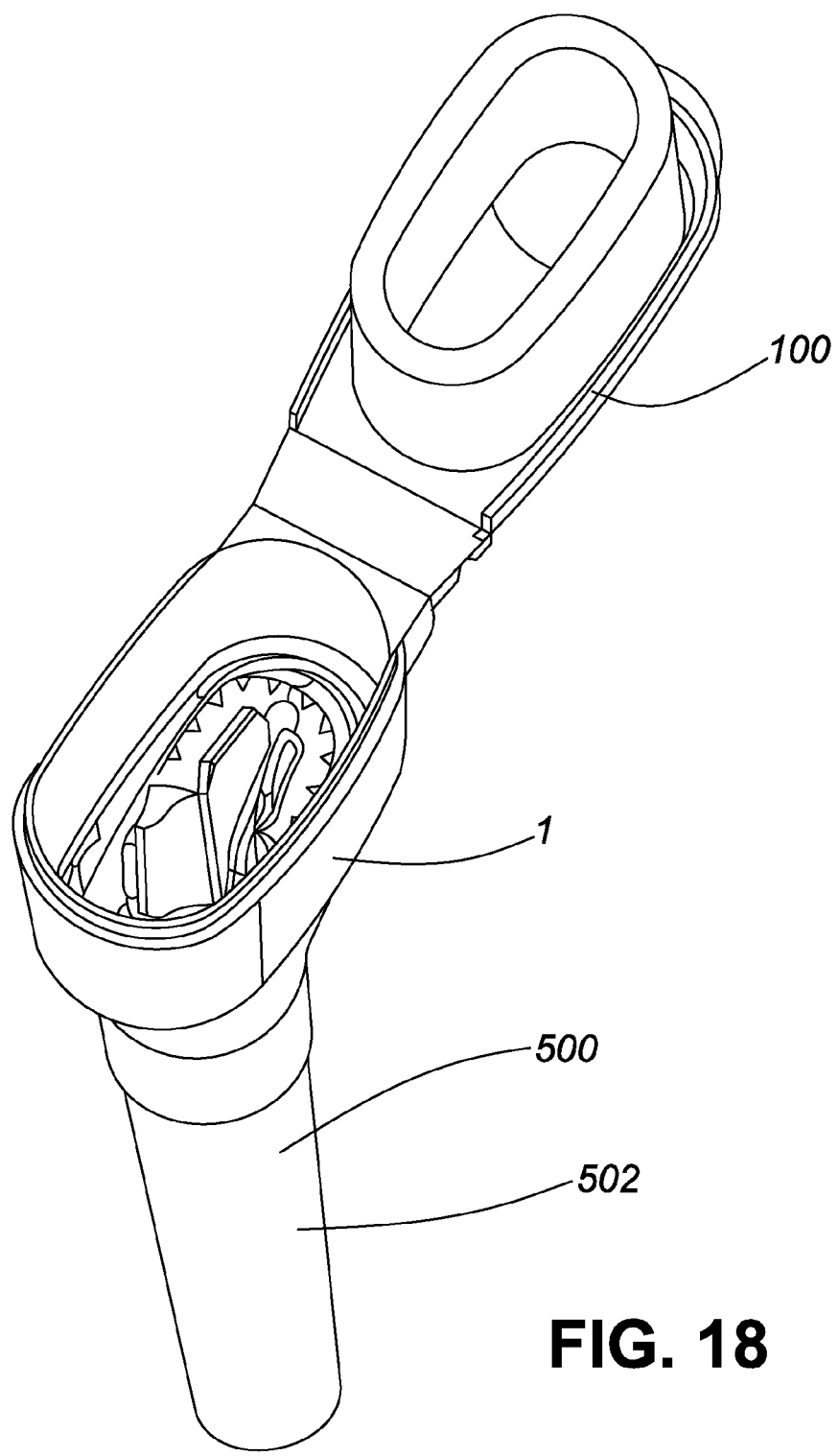
FIG. 18 is a perspective top view depicting another alternative embodiment of the sample receiving device of the present invention.
Figure 19:
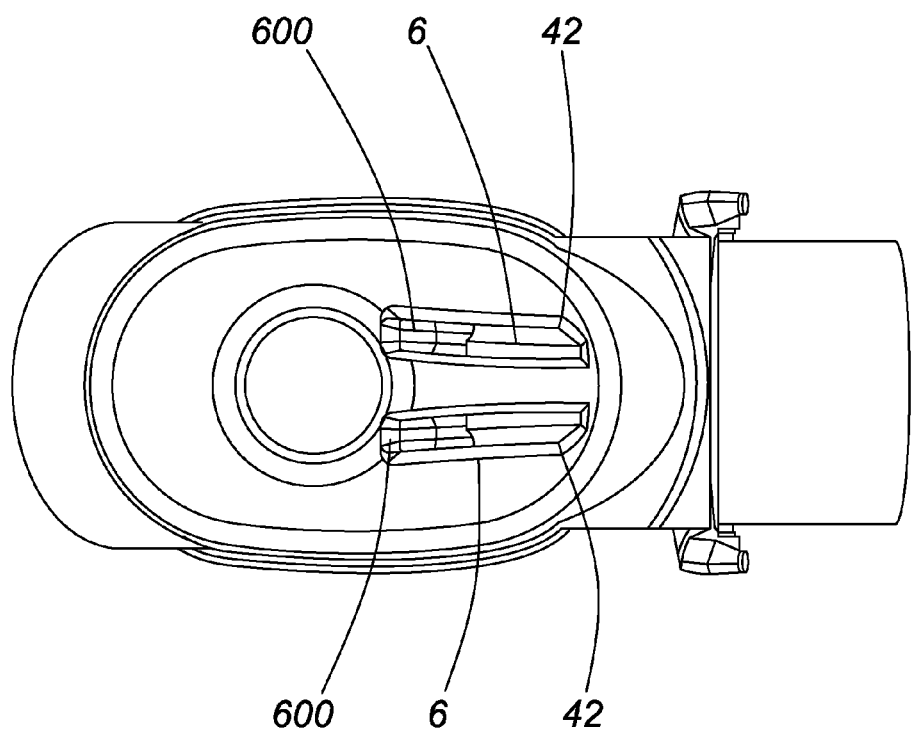
FIG. 19 is a top view of the sample receiving device of FIG. 5.
Figure 20A:
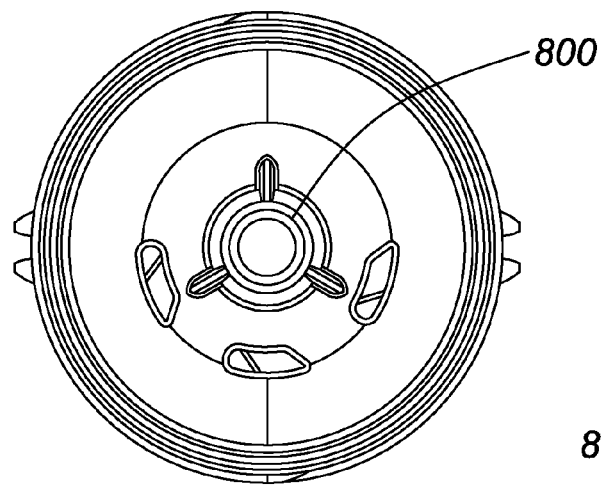
FIGS. 20A-20C is a top view and cross sectional view depicting one embodiment of a sample expelling mechanism of the present invention.
Figure 20B:
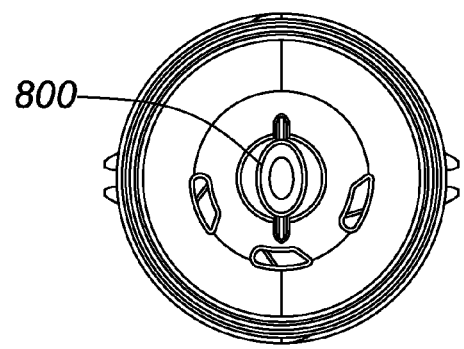
Figure 20C:
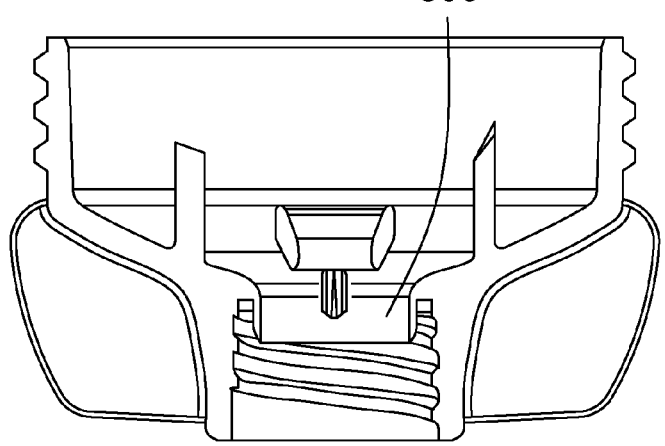
Figure 21A:
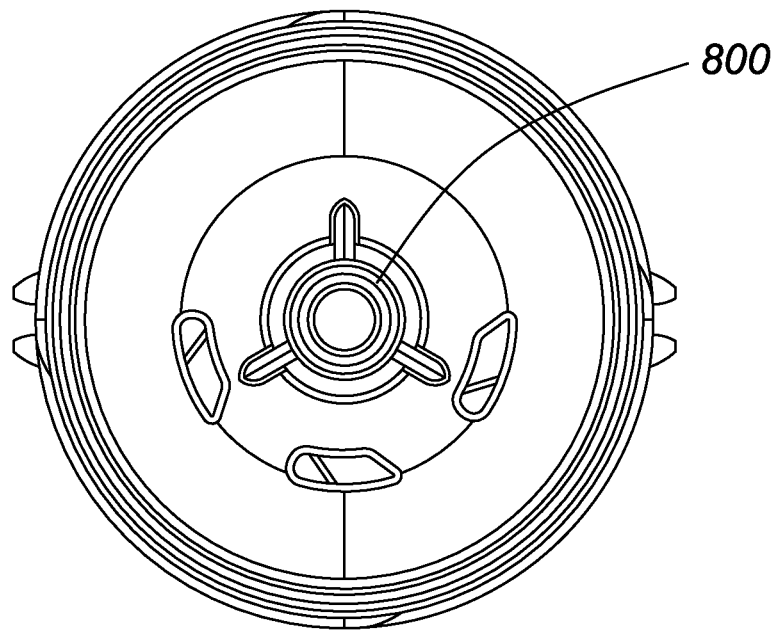
FIG. 21A is a top view and FIG. 21B is a cross sectional view depicting an alternative embodiment of a sample expelling mechanism of the present invention.
Figure 21B:
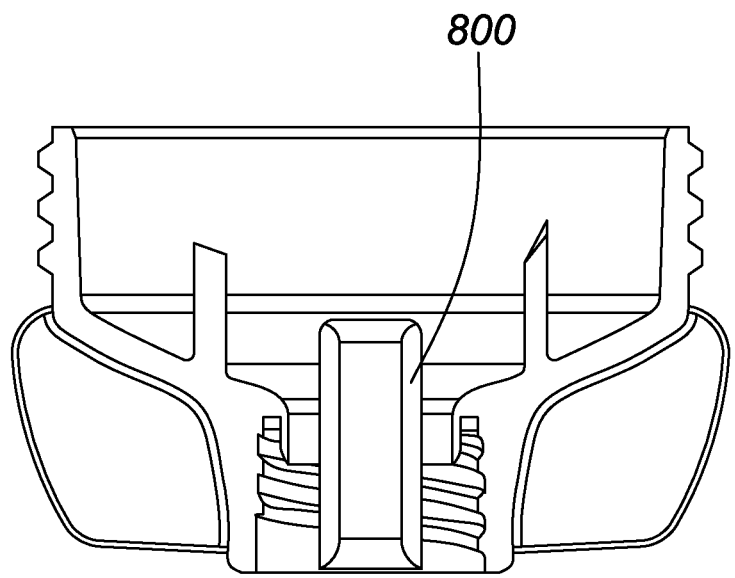

One cutting assembly arrangement is depicted in FIGS. 1A, 1B, 2 and 18, in which the tensioning means comprises two tension ribs 8 positioned centrally and projecting upward from the sloped bottom surface of funnel 1. Tension ribs 8 are of differing heights with the one closest to cutting rib 6 being taller and being of a height approximately equal to that of cutting rib 6. The specific heights are selected based on various parameters, including the film characteristics of permeable membrane 160. Also, as depicted in FIG. 18, as cutting proceeds, lid inner rib 108 moves into the space between tension ribs 8, thereby urging pierceable membrane 160 through a pathway that maintains a suitable tension of pierceable membrane 160 so as to facilitate piercing and propagation of the opening of pierceable membrane 160. Such a configuration facilitates sufficient disruption of pierceable membrane 160 so as to permit sufficient release of the substance from reservoir 102.

An alternative cutting assembly arrangement is depicted in FIGS. 5, 6A-6B, 8, 10 and 19-22B. In this example, funnel 1 comprises two cutting ribs 6, each of which comprises piercing tooth 42 and an integral tension rib 600 portion. The ribs include notch 602 between piercing tooth 42 and tension rib 600. In this example, as lid 100 and funnel 1 are moved to the piercing position, piercing tooth 42 of each cutting rib 6 begins to pierce and disrupt pierceable membrane 160. As cutting proceeds, tension rib 600 engages pierceable membrane 160, thereby maintaining suitable tension during cutting. It will be appreciated that near the end of disruption of pierceable membrane 160, the tension may be diminished such that no additional disruption occurs. However, at this point, pierceable membrane 160 is sufficiently disrupted so as to permit sufficient and/or timely release of the content of reservoir 104 in to interior chamber 2.

A preferred cutting assembly arrangement is depicted in FIGS. 32A-35B in which the combination of cutting rib 6, piercing tooth 42 and tension rib 8 forms a curved "V" shape forming a pocket region such that piercing tooth 42 is at the apex of the "V" at the end of funnel 1 closest to the hinge. The opposite end of the V forms an expelling means as described below. Piercing tooth 42 is positioned to be the first point of contact of the cutting assembly and pierceable membrane 160 during closing. The components of the cutting assembly in this arrangement are intentionally situated centrally in the open receiving end of the funnel so that the substance will evacuate reservoir 102 between cutting rib 6 and tension rib 8 to wash sample down into the tube from the funnel. This arrangement includes a number of optional configurations that can be used to optimize the cutting efficiency depending on the film characteristics of pierceable membrane 160. For example, in one embodiment, there is a notch 41 and piercing tooth 42 is a separate element. In an alternative embodiment, piercing tooth 42 forms part of cutting rib 6 without a notch therebetween (see, FIGS. 32A-32C).

Another optional configuration of the cutting assembly generally depicted in FIGS. 33A-35B is based on the selection of the relative heights of the cutting rib 6, piercing tooth 42 and tension rib 8. In one example (see, FIGS. 33A-33B), all three components are approximately the same height. In one advantageous example (see, FIGS. 34A-34B and 35A-35B), cutting rib 6 is raised with respect to tension rib 8. The increased relative height of cutting rib 6 should reduce the force required to cut the film and minimize uncontrolled cutting of pierceable membrane 160 by the blunt tension rib 8. Specifically, the blunt tension rib 8 will not engage (and stretch) the film as early as in the configuration in which it is the same height at cutting rib 6, thereby permitting piercing tooth 42 and cutting rib 6 to puncture the film and to start propagating the cut without interference from tension rib 8, while maintaining sufficient tension on the membrane during cutting to facilitate a controlled cutting process in which the film is cut along the entire length of the sharp cutting edge of cutting rib 6.

The sequence of cutting events will be generally as follows: first tooth 42 will puncture the film; cutting rib 6 will start to propagate the tear; tension in the film will progressively lessen as a result of the cutting; tension rib 8 starts to exert additional tension by pushing the film into the reservoir, thereby allowing cutting rib 6 to continue propagation of the tear. In some instances tension rib 8 will also cut the film, however, its primary function will be to maintain film tension during cutting as described herein.

The action of tension rib 8 should also widen the opening created by the cutting edge to ensure a rapid evacuation of the substance from the reservoir in the lid. Increasing the height of the cutting blade also provides more surface area and leverage for wringing sample from an absorbent sample collection tool, such as a sponge or foam swab. In examples in which the cutting rib and the tension rib were the same or similar height, the entire length of the absorbent (e.g., foam) tip may not fit inside the 'pocket' created by the tension rib and cutting rib, so sample expelling efficiency was not maximized near the exposed handle of the collection tool. The expelling means are described in more detail in the following section.

Tension rib 8, in cooperation with lid inner rib 108 in lid 100, functions to widen the opening in the film created by the single cutting rib 6. It is not sufficient to simply poke a hole(s) or slice the film since, in order for the substance to drain quickly from the reservoir, the opening of the film must be wide/catastrophic. A wide opening 'allows' air to quickly enter the reservoir and the substance, in turn, is rapidly evacuated from the reservoir.

Sample Expelling Means

As discussed supra, sample receiving device 200 is configured for collection of a variety of substances, including a biological sample. In one example, sample collection is achieved by direct collection of the sample into the sample receiving device. For example, a subject directly deposits the sample in the device. However, in some instances, it may be advantageous or necessary to use a sample collection tool to collect the sample, and subsequently deposit the collected sample in the receiving device 200.

In one embodiment of the invention, a sample is collected using a sample collecting tool (not shown) that comprises a non-absorbent member used to collect/transfer a sample into receiving device 200. For example, a biopsy/scraping of tissue/skin, fine needle aspirates, discharge, cells grown in culture, bodily fluids and secretions, hairs, scrapings from cell membranes and the like can be transferred into collection device 200.

In an alternative embodiment (see, for example, FIG. 5), a sample is collected using sample collecting tool 400, which comprises absorbent member 402 and handle 404. Non-limiting examples of an absorbent member include a cotton swab, a flocked swab, a polyester swab, a rayon swab, a microfiber swab, a foam swab, an Aquazone™ swab or sponge and the like, which would be well known to the skilled worker. It will be appreciated the sample collected can be placed in either (i) a sample collection device of the present invention in which lid 100 and funnel 1 have not yet been moved to the closed position, or (ii) a collection device in which lid 100 and funnel 1 have been moved to the closed position, thereby releasing the contents of reservoir 102, and then moved back to the open position. The second (ii) example can also be referred to as "pre-triggering" collection device 200.

By pre-triggering the device, the substance released from reservoir 102 into the vial 500 is used to help expel, recover or extract the sample collected from any of the sample collection devices. For instance, a sample collected from a nasal cavity with an absorbent member (e.g., foam sponge) may not be readily expelled into the device using the sample expelling means of the present invention (as defined further below) due to the small volume of sample collected, the mucinous and viscous nature of the nasal sample, and or absorptive nature of the absorbent member. Wetting the sample-containing absorbent member in the substance already released into the vial/tube can facilitate recovery of the sample. Specifically, the sample-containing absorbent member can be plunged up and down in the substance to facilitate release and recovery of the sample into the device. The sample plus substance mixture remaining in the absorbent member can then be expelled and recovered from the foam using the sample expelling means.

In one example, the absorbent member-containing biological sample is removed from the handle and deposited within the collection device. In this example, the absorbent member is cut, for example using scissors, and deposited directly into the collection device. Alternatively, or in addition to, the sample collection tool can include a break point/score/feature between the absorbent member and the handle member, wherein a user is able to detach the absorbent member from the handle and deposit the absorbent member into the collection device.

In another example, it may be desirable or necessary to obtain a biological sample using a collection device comprising an absorbent member and a handle, and subsequently expel or recover the biological sample from the absorbent member, rather than depositing the absorbent member into the collection device. In this example, collection device 200 further comprises a sample expelling means configured to expel the biological sample from biological sample-containing absorbent member within the interior chamber of funnel 1. The expelling means can be integral or removably attachable to collection device 200. Furthermore, the expelling means can be integral to or separate from the cutting assembly. Preferably, the integral expelling means does not obscure flow path 22 of funnel 1.

In each case, the sample expelling means of the present invention comprises a compression element configured to permit manual compression of the absorbent member so as to expel the biological sample through interior channel 2 of funnel 1 and into the sample receptacle (e.g., vial or tube). The compression element can be selected to facilitate release of samples having various viscosities. The compression element can be a variety of shapes, for example, it can be a V-shaped, U-shaped, horseshoe-shaped, straight, chamfered, cylindrical, cone-shaped, screw-shaped, bladed, combinations thereof, and the like.

To collect a biological sample, a sample such as a liquid sample, is collected by wicking the liquid into absorbent member (mopping up the sample), by contacting the absorbent member to a liquid sample. The absorbent member can be made from a variety of absorbent materials. In one example the absorbent member is formed and cut to the desired size. In one example the absorbent member is moulded to the desired size. The material of the absorbent member will vary according to the intended use In one example, the absorbent member is a sock style foam mitt made from 100 PPIZ reticulated polyurethane open cell foam. As will be appreciated by the skilled worker, multiple types of manufactured foams are suitable, for example, reticulated/non-reticulated, open cell/closed cell, and a range of PPI (pores per square inch). Cotton, AquaZone™, polyester, rayon, gauze and nylon fibers (flocked swabs) are also materials commonly used in the manufacture of absorbent members. Nylon fibers are not very absorbent. It was found that wrapped cotton (Q-tip) and gauze are absorbent, but did not readily release cells/DNA into the substance. Handles are typically made from moulded or extruded polypropylene, but polystyrene, polyolefin, nylon, aluminum, glass, glass-filled nylon, paper or wood are also acceptable.

After a sample is collected by the absorbent member, the collection tool is placed in the collection device and the absorbent member is compressed against the compression element. As the absorbent member is compressed against the compression element the sample is expelled. The compression of the absorbent member against the compression element can be, for example, done by way of a "wiping action" as the absorbent member is drawn along all or a portion of the compression element. Alternatively, compression is achieved as the absorbent member is twisted/rotated (e.g., using a "wringing action") as it is drawn through the compression area to effectively wring the sample out of the absorbent material.

It will be appreciated that the absorbent member can be repeatedly drawn through, or twisted against, the compression element to expel as much of the sample from the absorbent member as desired or as is possible. It will also be appreciated that, depending on the application, a sample can be collected on the absorbent member, the sample expelled from the absorbent member and additional sample can be collected and expelled, using the same absorbent member or a new absorbent member, from the same or different source. Vial 500 may be labelled or marked with a line indicating the volume/amount of sample to be collected.

In the Example of FIGS. 19 and 31A-35B, the sample expelling means comprises compression element formed by cutting and/or tension ribs extending upward from the bottom interior surface of funnel 1. The ribs are positioned in a generally V-shaped configuration in the open receiving end of funnel 1, providing a narrow end and wide end. In this example, the ribs are also angled outwardly relative to one another. In this configuration the ribs define the compression element and provide a channel within which to draw the collection tool during the expelling process, and permit a range of differently sized absorbent members to be used within the compression area.

For example, when the ribs are askew, a user is able to draw an absorbent member-containing a biological sample through the wide end (closest to flow path 22) towards the narrow end (closest to the hinge) of the compression element defined by the ribs. As the absorbent member is drawn through the compression area, the absorbent member is compressed and the biological sample contained within the absorbent member is expelled from the absorbent member into the interior chamber 2 of funnel 1.

Positioning of the ribs outwardly with respect to one another (i.e., V-shaped) permits a range of differently sized absorbent members to be used. For example, a smaller absorbent member will fit between the ribs at a position closer to floor of the funnel than would a larger sized absorbent material. A smaller absorbent member will also fit between the ribs at a position closer the narrow end defined by the ribs, than would a larger sized absorbent member. As above, pulling the absorbent member from the open end towards the narrow end causes the biological sample to be expelled. The ribs can be a variety of shapes, and may be the same or different sizes. Ribs 8 can be made from a variety of materials, depending on the needs and preferences of the user and/or manufacturer.

FIGS. 20A-20C and 21A-21B depict an alternate example of the expelling mechanism. In this example, the expelling mechanism comprises generally cylindrical member 800 having a through passage defining the compression area and the channel. Cylindrical member 800 is positioned to surround all or a portion of flow path 22 of funnel 1. The generally cylindrical member is sized such that passing a sample-containing absorbent member along the through passage causes the absorbent member to be compressed, and the biological sample to be expelled. Cylindrical member 800 can be a variety of shapes and configurations. In one example cylindrical member 800 has generally the same interior diameter along its length. It will be appreciated that cylindrical member 800 can have a relatively wider first open end than the second open end, e.g., it is tapered. This taper facilitates the use of differently sized absorbent members. It will be appreciated that the length of the cylinder member can vary. FIGS. 26A-26D and 27 show cylindrical members 800 of differing length.

Figure 22A:
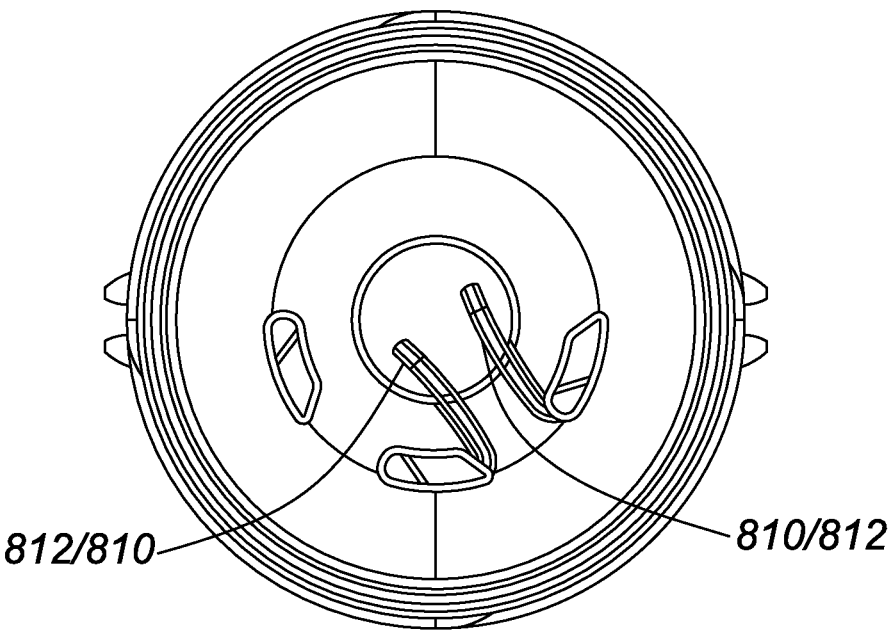
FIG. 22A is a top view and FIG. 22B is a cross sectional view depicting another alternative embodiment of a sample expelling mechanism of the present invention.
Figure 22B:
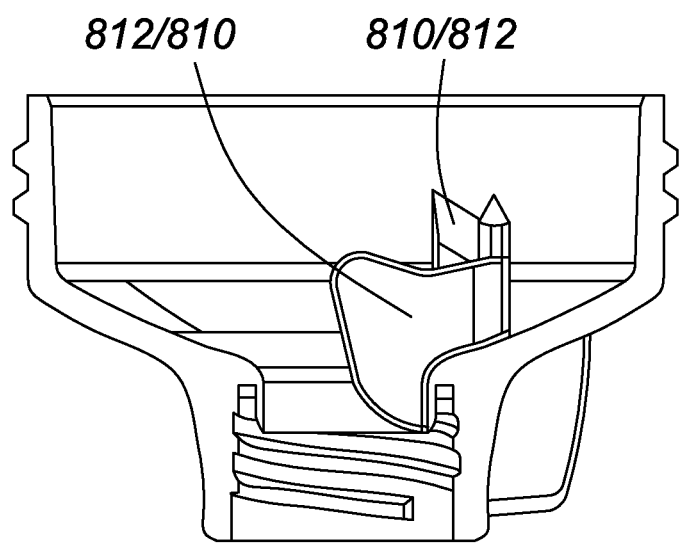

FIGS. 22A-22B depict an alternate example of the expelling means. In this example the expelling means comprises rib 810 and rib 812 spaced apart, defining a compression area and a channel. Rib 810 and rib 812 each comprise a first end attached to the interior surface of funnel 1 and a second end. Rib 810 and rib 812 are generally parallel or askew, relative to one another, and are configured to expel a biological sample from an absorbent member-containing biological sample when the absorbent member is pulled though the compression area.

Figure 23A:
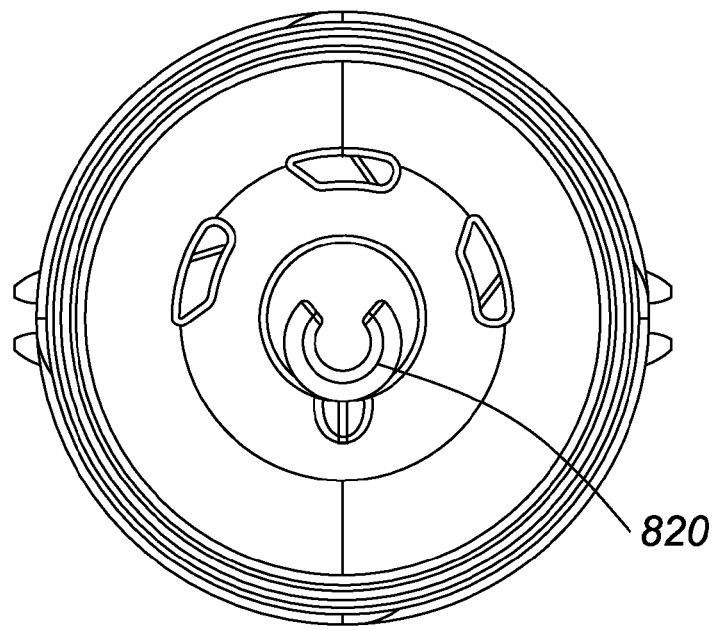
FIG. 23A is a top view and FIG. 23B is a cross sectional view depicting another alternative embodiment of a sample expelling mechanism of the present invention.
Figure 23B:
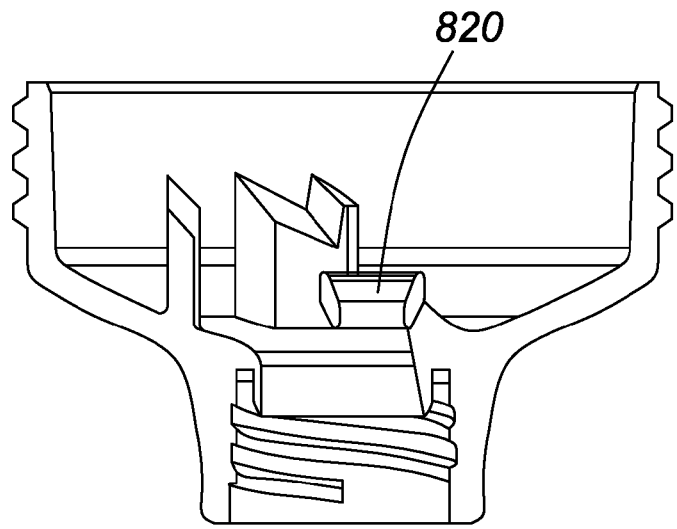

FIGS. 23A-23B depict an alternate example of the expelling means. In this example expelling means comprises semi-circular member 820 defining a compression area and a channel. In this example, the wall of semi-circular member 820 is angled such that the first end of the semi-circular member is larger than the second end. This relative difference in the size for the diameter of the passage facilitates the use of differently sized absorbent members. It will be appreciated that semi-circular member 820 in which the inner diameter is generally the same along the passage may also be used.

Figure 24A:
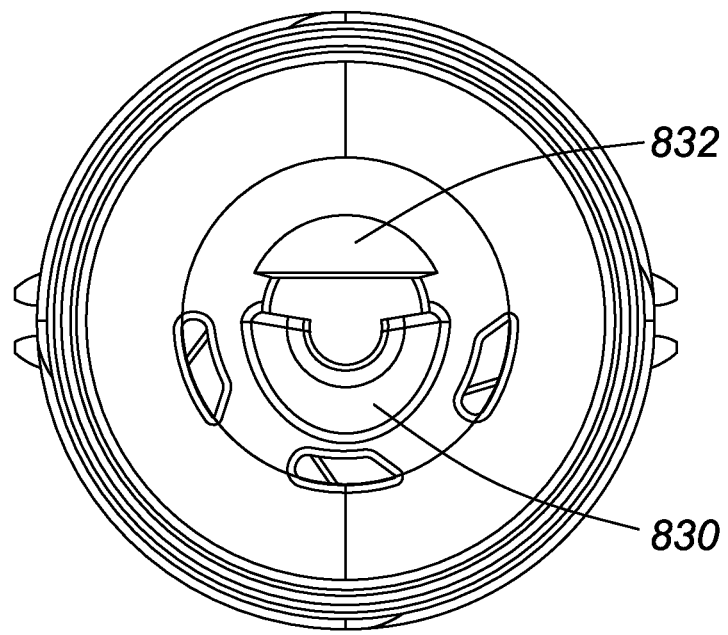
FIG. 24A is a top view and FIG. 24B is a cross sectional view depicting another alternative embodiment of a sample expelling mechanism of the present invention
Figure 24B:
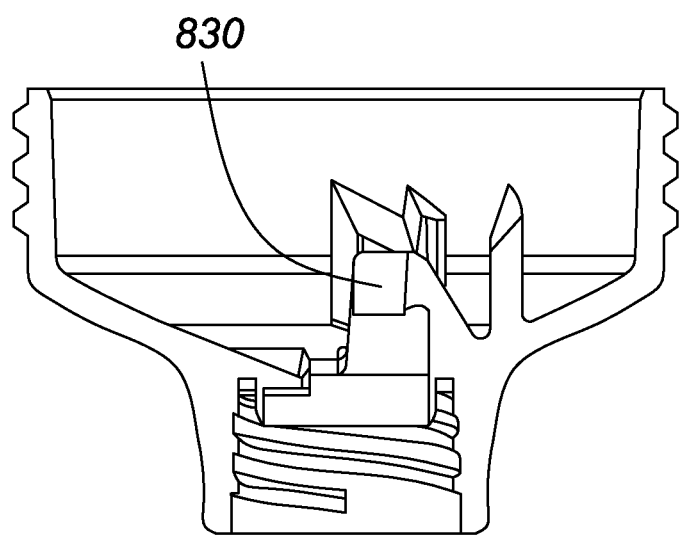
Figure 25A:
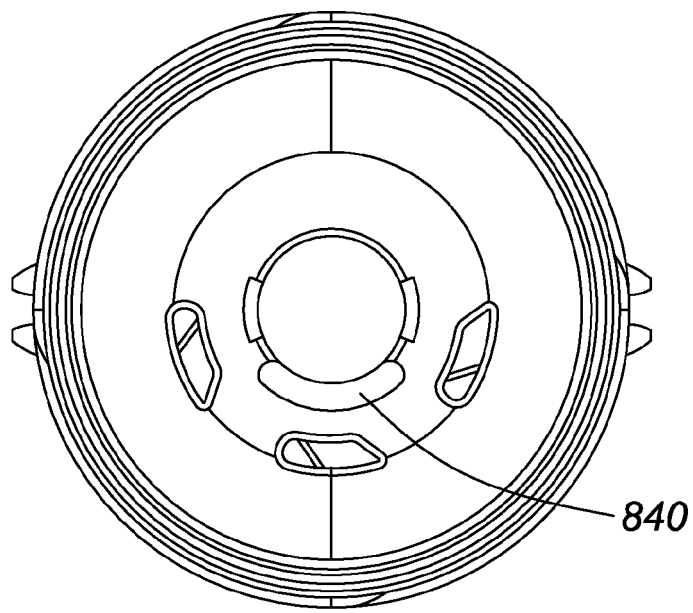
FIG. 25A is a top view and FIG. 25B is a cross sectional view depicting another alternative embodiment of a sample expelling mechanism of the present invention.
Figure 25B:
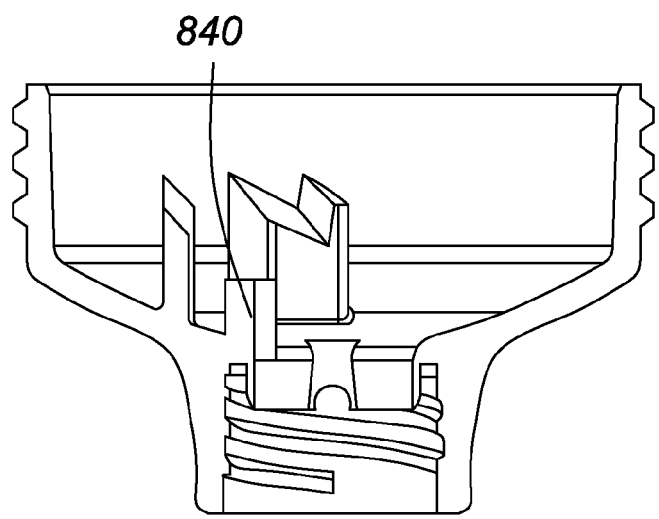

FIGS. 24A-24B depict an alternate example of the expelling means. In this example the expelling means comprises first semi-circular member 830 and second blade member 832, each attached to the interior surface of funnel 1 and positioned generally opposite one another. First semi-circular member has second end attached to the interior surface of the funnel and a first end, generally smaller in diameter than the second. Insertion of the absorbent member into the through channel and pulling it out, against the blade portion expels the biological sample from the absorbent member.

FIGS. 25A-25B and 26A-26D depicts an alternate example of the expelling means. In this example the expelling means comprises first member 840 attached to the inner surface of funnel 1 and expelling clamp 842. Expelling clamp 842 is removably attachable to the interior of a funnel, generally at the second open end of the funnel. Clamp 842 comprises first end handle 844 and a second end configured for removable attachment to the interior of funnel 1. In the example of the Figures, the second end comprises prong members 846 adapted to engage the interior walls of the funnel. When clamp 842 is attached to the funnel, the second end of clamp 842 and first member 840 define the compression area and channel.

Figure 27:
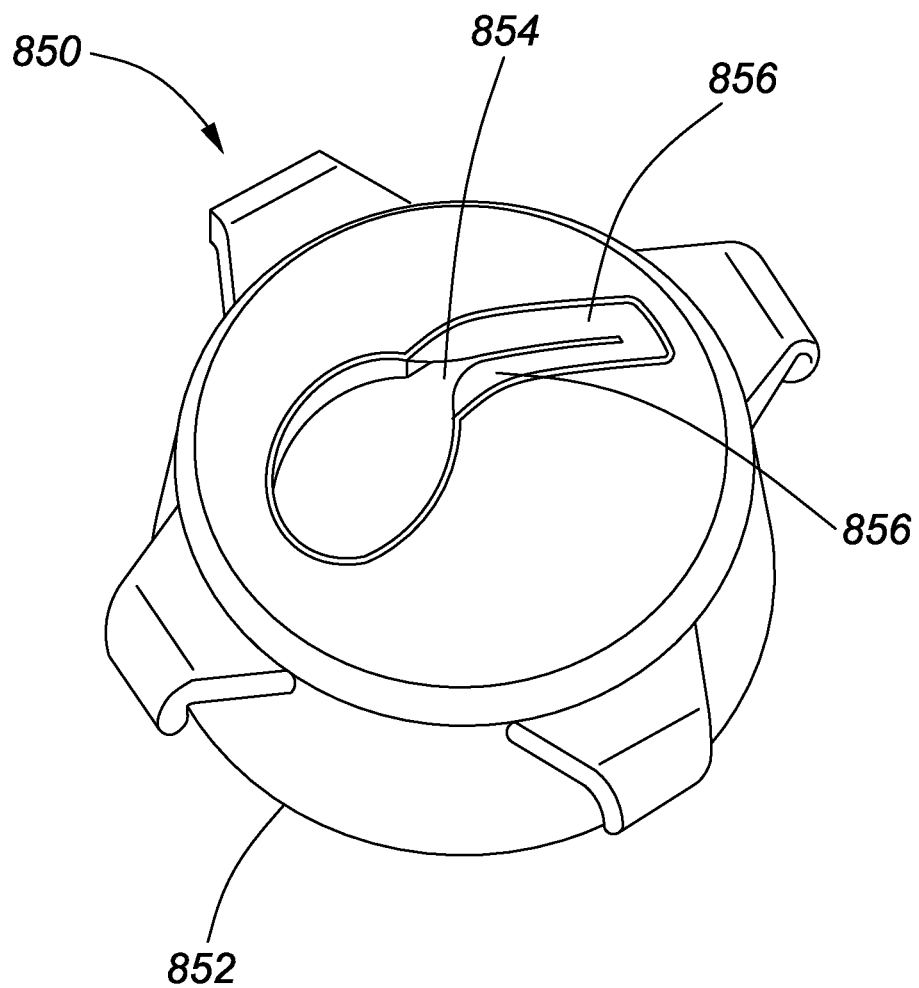
FIG. 27 depicts an expelling cover that acts as a sample expelling mechanism according to another embodiment of the present invention.
Figure 28A:
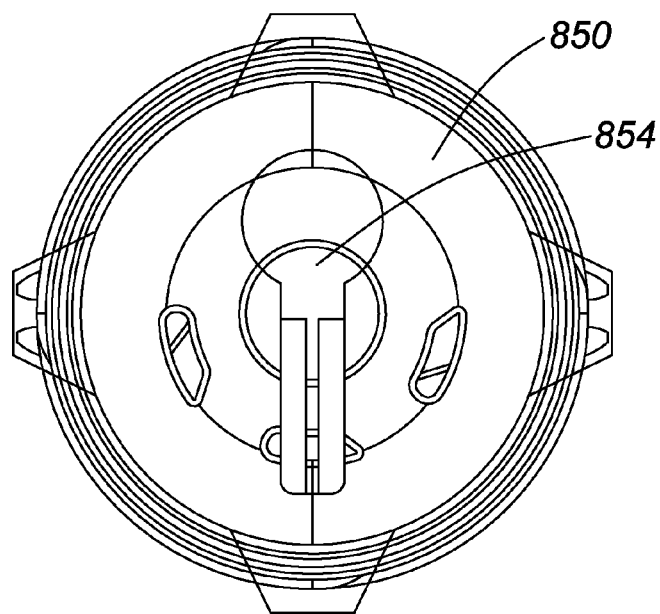
FIG. 28A is a top view and FIG. 28B is a cross sectional view depicting the expelling cover of FIG. 27 in operative association with a sample receiving device.
Figure 28B:
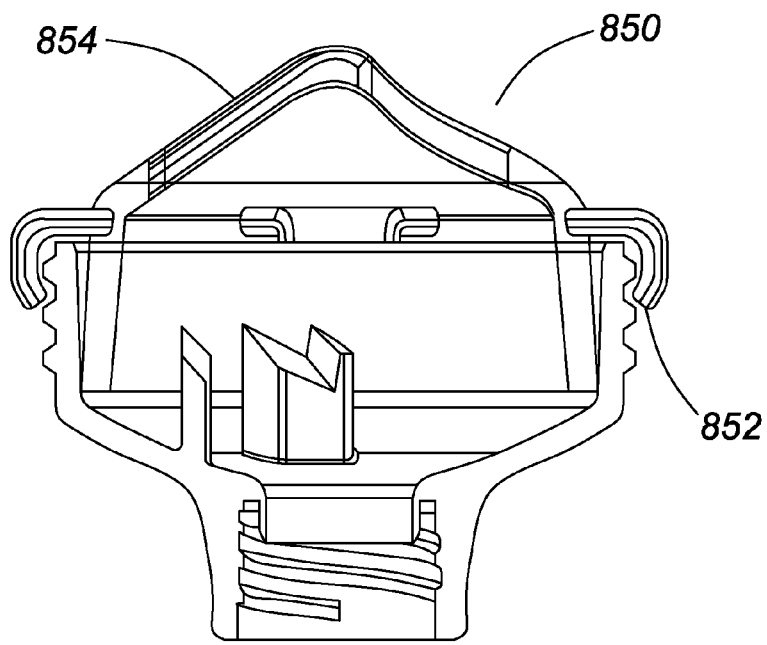

FIGS. 27 and 28A-28B depict an alternate example of the expelling means. In this example the expelling system comprises expelling cover 850 removably attachable to the open end of a sample receiving funnel. Expelling cover 850 comprises an open portion configured for removable attachment to the open receiving end of a funnel and a cover portion having an opening (854) therethrough that includes a slot with two pliable flanges (856) defining the compression area and channel. As shown in the figures the expelling cover includes latching tabs 852 that interact with the outward edge of the funnel to retain the expelling over in place during sample terminal.

Figure 34A:
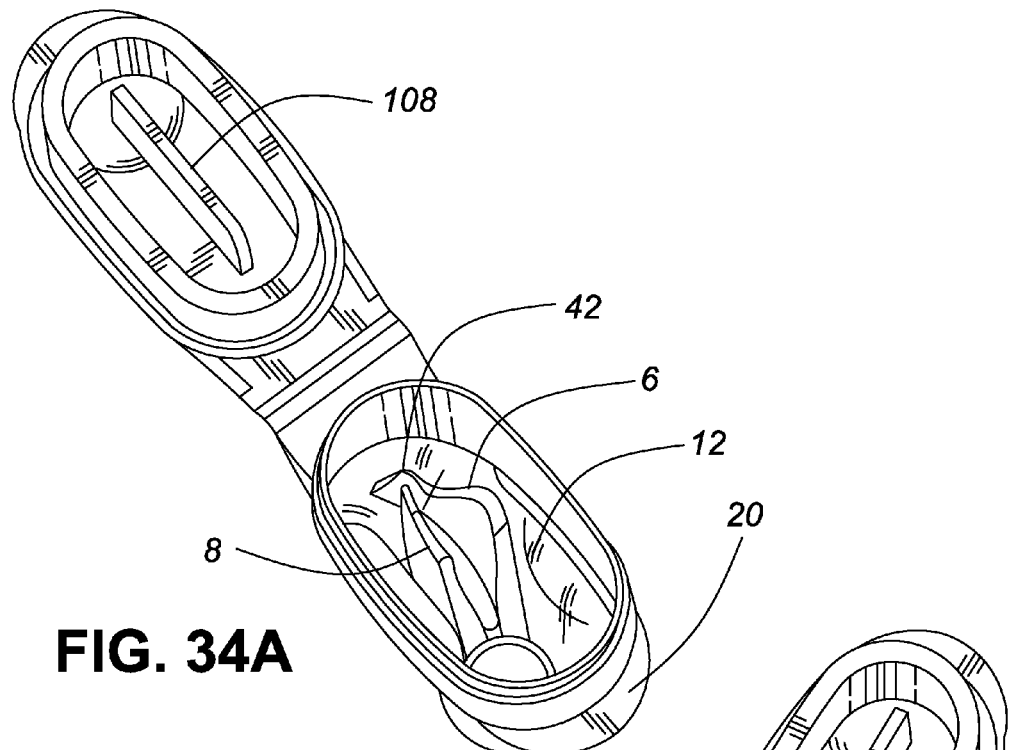
FIGS. 34A-34B depict top, left and right side perspective views of a sample receiving device in accordance with another alternative embodiment of the present invention, which includes a raised cutting rib.
Figure 34B:
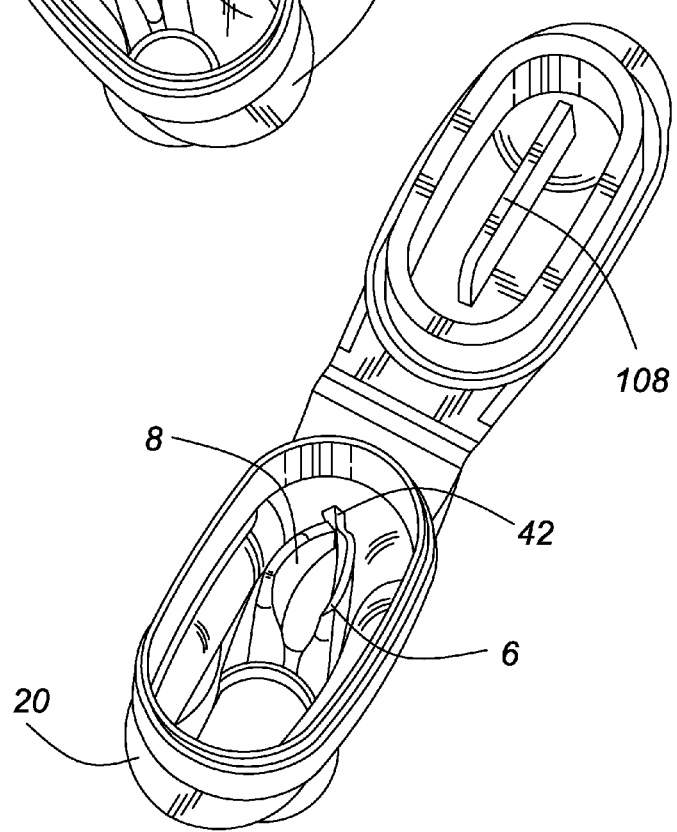

FIGS. 34A-34B depict an example of a preferred sample expelling means. In this example, the cutting assembly is configured such that the tension rib 8, cutter rib 6 and piercing tooth 42 are arranged in a "V" shape that forms a pocket with piercing tooth 42 at the apex of the "V" and the opposite end of the pocket being open. The boundary of the open end of the "V" is defined by the vertical/terminal edges of the cutting rib 6 and tension rib 8, closest to the throat of the funnel channel 2. These terminal edges include flanges that extend inwardly to provide additional compression area for compression of the absorbent portion (e.g., sponge) of the collection tool when it is placed within the pocket and drawn through or wrung against the two terminal edges and inward facing flanges to expel sample from the absorbent portion of the tool, which then flows down into channel 2 as a result of the downward slope of the bottom surface of the funnel. In the case in which cutting rib 6 is raised with respect to tension rib 8, the terminal edges of the ribs will be modified to continue the inward flanges upward on both terminal edges of cutting rib 6 and tension rib 8. This modification can enhance the recovery of sample while wringing the sponge against an inner surface of cutting rib 6 or tension rib 8 of the expelling means. The opening at the base of the expelling means is configured to ensure that sample flow into channel 2 is not hindered.

In the most preferred embodiment of the invention, the sponge of the collection tool is placed upright (foam tip down) within the 'pocket' and wrung (like a mop) or twisted while maintaining the sponge handle in a substantially vertical position. The flanges on the terminal edges of cutting rib 6 and tension rib 8 provide additional surface area for compression of the absorbent portion (e.g., foam or sponge) and function like wiping blades; that is they scrape, or wipe, the sample off the absorbent portion as it is expelled, thereby facilitating the transfer of sample into the channel 2.

Sample Receptacle

In one embodiment of the present invention, the sample receiving system includes a removable sample receptacle, such as a vial or tube, which is suitable for subsequent processing of samples and/or for use in robotic systems. In one example, due to the size and shape, the container system is readily transported or shipped by mail and stored in standard/common racks.

As depicted in the figures, vial 500 is generally cylindrically shaped with an open end for removable or fixed attachment to the second end of funnel 1, and chamber 530 for receiving a sample. It should be appreciated, however, that vial 500 can be a variety of shapes, as determined by the needs or preferences of the user and/or application of use, and can be specifically manufactured for use in the sample receiving system of the present invention or can be a commercially available vial. As noted above, and in one embodiment, funnel 1 is integral with vial 500. When the container system is used for laboratory purposes, desirably, vial 500 is sized to fit within a standard test tube rack such as that typically used in biological sample processing. In one example, vial 500 conforms to industry-standard dimensions for blood collection tubes (e.g., 13 mm×75 mm). Advantageously, vial 500 is suitable for use with robotic DNA purification systems (e.g., the Beckman BioMek™ FX or a liquid-handling robot from Tecan Group Ltd., such as the Freedom EVO® series). One example of such a vial is commercially availably from Simport Plastics Limited (e.g., the T501 tubes), however, multiple examples of such tubes are currently on the market.

Additionally, one example of the system of the present invention includes vial 500 having a false bottom. The use of such a false bottom is well known and can be utilized to ensure that the sample mixture within the vial is at a height suitable for automated analysis or processing. In a specific example, vial 500 is a 5 ml conical false bottom tube from Sarstedt, Inc. (e.g., 15.3 mm×92 mm; Cat No 60.611.010).

Vial 500 may be removably attached to funnel 1 using a variety of securing mechanisms. In accordance with one embodiment of the present invention, the securing mechanism is a helical threaded screw. Alternatively, the securing mechanism is a snap-fit or stopper-fit. Alternatively, vial 500 is fixedly attached to, or integral with, funnel 1.

In accordance with one embodiment of the invention, the sample receptacle can be attached to the second end of the funnel via a 'universal adapter' for removable or fixed attachment to the funnel at one end and vial/tube 500 at the second end. The use of such adapter(s) would allow one to utilize the device of the present invention with tubes/vials of numerous different and perhaps non-standard diameters (e.g., 13 vs. 16 mm) or tubes/vials with different threads or attachment features (e.g., stopper), without the need for costly changes to the mould for the funnel/lid assembly.

Typically, the open end of vial 500 includes securing means for closure using a standard cap 66 following collection of a sample, release of the substance from reservoir 102 and removal of the sample receiving device (i.e., lid and funnel assembly). Cap 66 can be secured by via threaded screw, snap-fit, push-fit and the like. Vial 500 optionally includes surface 502 that is suitable for labelling and/or barcoding and/or for providing friction for gripping by a user.

In accordance with one embodiment of the present invention, the sample receiving system includes a cap for closing the sample receptacle following sample collection and removal of the sample collection device (i.e., the funnel and lid assembly). In one example, cap 66 is stored in the open receiving end of funnel 1. In this example, one or more interior surfaces within the open receiving end of funnel 1 can include a receiving indentation sized to receive cap 66 within funnel 1. For example, in FIG. 3B one receiving indentation 12 is on the inner facing side surface of cutting rib 6 and a second receiving indentation is positioned opposite the first indentation on the inner surface of the funnel wall. Alternatively, as depicted in FIGS. 32A-34B, funnel 1 includes two receiving indentations 12 that are facing one another and are made in the sloped side walls of funnel 1 adjacent the opening to channel 2. When cap 66 is positioned within funnel 1 using receiving indentations 12 a user is prevented from moving lid 100 so as to disrupt pierceable membrane 160. In a specific example, the receiving indentations are configured to receive caps suitable to use with both 13 mm and 16 mm tubes/vials.

In an alternative embodiment of the invention, the sample collection system includes a captive cap which is removably attached via a retaining member. For example, a cap can be integrally connected to a strap or tether which can be or is connected to the vial or tube so that when the cap is not used to close from the mouth of the vial or tube, the cap remains tethered to the container by the strap. This type of container and tethered cap is disclosed in, for example, U.S. Pat. No. 2,958,439, U.S. Pat. No. 3,419,179 and U.S. Pat. No. 3,799,426. Other examples of vials with captive caps that are suitable for use in the sample receiving system of the present invention are of the type disclosed in U.S. Pat. No. 4,753,358, which include a slide ring that fits about a generally cylindrical vial or tube and has an integral strap or tether to which is attached a cap. The slide ring permits rotation of the cap in the case where the cap and vial are designed for threaded engagement in order to seal the opening of the vial.

When incorporated in a specific example of the system of the present invention, the funnel/lid assembly would be threaded onto a 13 or 16 mm tube with this type of cap in place, making it more obvious to the user (and more convenient) that the funnel needs to be removed after triggering the system in order to cap the tube containing the sample and substance mixture. Also, a captive cap of this type would not need to be managed in a particular packaging.

Disruption of Pierceable Membrane

As described above, lid 100 and funnel 1 interact and are movable between an open position and a closed position. In the open position, interior channel 2 is maintained out of fluid communication with the contents of reservoir 102 by pierceable membrane 160. In the closed position, interior channel 2 is sealed against leakage to the outside of the sample receiving device.

With reference to the figures, movement of lid 100 and funnel 1 from the open position to the closed, piercing position, results in cutting of pierceable membrane 160 by piercing tooth 42 (when present) and cutting rib(s) 6, with consequent release of the substance within reservoir 102 into vial 500 via interior channel 2. In operation, in moving lid 100 to the closed position, piercing tooth 42 is first brought into contact with pierceable membrane 160 and pierces pierceable membrane 160. Continued closure moves piercing tooth (or teeth) 42 through pierceable membrane 160, disrupting pierceable membrane 160, and thereby producing an opening in the sealing membrane to enable the substance to enter chamber 2. A cut is propagated from this hole by the action of cutter rib(s) 6 as lid 100 continues in its closing motion.

It will be clear to the skilled worker that length, height, rigidity, sharpness of piercing tooth 42, and of cutting rib(s) 6 are selected (and carefully positioned within funnel 1) such that they efficiently disrupt pierceable membrane 160 when lid 100 and funnel 1 are in the closed, piercing position, and do not disrupt the pierceable membrane 160 when lid 100 and vial 1 are in the open position. Selection of these parameters will be based on a number of considerations, including, the intended use of the system and the nature of the pierceable membrane.

Applications of the Sample Receiving System

According to one embodiment of the present invention, the container system of the present application is suitable for releasably storing one or more compositions intended to stabilize, preserve, or recover one or more components of a biological sample such as a bodily fluid and/or tissue. In a specific embodiment of the invention, one of said one or more compositions is suitable for preserving and storing biomolecules, such as nucleic acids and proteins.

Desirably, funnel 1 is sized for collecting a biological sample. The sample is obtained from a variety of sources and/or subjects. Non-limiting examples of biological samples include skin, hair, fecal matter, bodily fluids, tissue, cultured cells, collected cells and the like. Additional non-limiting examples include water or other fluid samples for analysis. For example, water samples containing bacteria, parasites or other contaminants present in drinking/well water and/or food products, infectious agents (e.g. virus and bacteria) on surfaces, etc. can be collected and stored through the use of the present sample receiving system.

Examples of compositions that can be stored in the collection device of the present invention include compositions for brief or prolonged storage, transport, and extraction, of nucleic acids and proteins from bodily fluids or secretions such as saliva, nasal secretions, semen/sperm, blood, vaginal secretions and/or tissues and/or microorganisms and/or infectious agents, wherein the nucleic acid in the resulting composition remains stable at room temperature for extended periods of time or until analysis can be performed. Additional examples can include compositions for collecting and, optionally storing and/or transporting samples containing analytes, chemicals (e.g., drugs of abuse, therapeutic drugs, elements/metals such as lead, etc.), contaminants, carbohydrates, steroids, etc.

The term "bodily fluid", as used herein, refers to a naturally occurring and/or secreted and/or excreted and/or discharged fluid and/or wash fluid from the surface or inside the bodies of a human or an animal, and includes, but is not limited to saliva, sputum, serum, blood plasma, blood, pharyngeal, nasal/nasal pharyngeal and sinus secretions, urine, mucous, gastric juices, chyme, vomit, pancreatic juices, bone marrow aspirates, cerebral spinal fluid, feces, semen/sperm, products of lactation or menstruation, amniotic fluid, aqueous humour, vitreous humour, cervical secretions, vaginal fluid/secretions, tears, bronchial lavage, pleural fluid, pus, sweat and lymph.

The terms "bodily tissue" "tissue", as used herein, refer to an aggregate of cells usually of a particular kind together with their intercellular substance that form one of the structural materials of a plant or an animal and that in animals include connective tissue, epithelium, mucosal membrane, muscle tissue, placental tissue, liver tissue, and nerve tissue, and the like. Samples of bodily tissue can be obtained by a variety of non-limiting methods, such as fine needle aspirates, scrapings or biopsy tissue. The term "tissue" can be used to refer to naturally occurring tissue or synthetic tissue.

The term "nucleic acid", as used herein, refers to a chain of nucleotides, including deoxyribonucleic acid (DNA) or ribonucleic acid (RNA), typically found in chromosomes, chromatin, mitochondria, ribosomes, cytoplasm, nucleus, microorganisms (e.g., bacteria) or viruses.

The term "ribonucleic acid" or "RNA", as used herein, refers to a wide range of RNA species, including, but not limited to high molecular weight RNA, large and small ribosomal RNAs, messenger RNA, pre-messenger RNA, small regulatory RNAs such as microRNA, RNA viruses (single and double-stranded, positive stranded or negative stranded) and the like. The RNA may be from a variety of sources, including, but not limited to human, non-human mammal, other animals, plant, viral, bacterial, fungal, protozoan, parasitic, single-celled, multi-cellular, in vitro, in vivo, ex vivo, natural, and/or synthetic sources.

The term "saliva", as used herein, refers to the secretion, or combination of secretions, from any of the salivary glands, including the parotid, submaxillary, and sublingual glands, optionally mixed with the secretions from the numerous small labial, buccal, and palatal glands that line the mouth. Included within the term "saliva" is gingival crevicular fluid or oral mucosal transudate (OMT), the fluid derived from the passive transport of serum components through the oral mucosa into the mouth.

The term "sputum", as used herein, refers to mucoid matter contained in or discharged from the nasal or buccal cavity of a mammal or other animal, including saliva and discharges from the respiratory passages, including the lungs.

The term "subject", as used herein, refers to a variety of organisms/sources, including, but not limited to human, non-human mammals, other animal species, viral, bacterial, fungal, protozoan, parasitic, single-celled, multi-cellular, in vitro, in vivo, natural, and/or synthetic sources. Specific non-limiting examples of suitable subjects include human, non-human primates, and bovine, canine and avian sources. Specific non-limiting examples include beef cattle, dairy cattle, sheep, goats, hogs, poultry, rodents and horses. Specific non-limiting examples also include companion animals, such as dogs, cats and the like.

The term "prolonged storage" refers to storage for at least about one day, two days, three days, four days, six days, one week, two weeks, three weeks, four weeks, five weeks, six weeks, seven weeks, or eight weeks, from about one day to about eight weeks, or greater than about eight weeks, about one year.

In use, a substance, such as a composition intended to stabilize, preserve, or facilitate the recovery of biomolecules, for example, nucleic acids, from a biological sample is sealed within reservoir 102 with a pierceable membrane. Suitable compositions include those described in International PCT application WO 2003/104251; International PCT application PCT/CA2006/000380; and International PCT application PCT/CA2007/001785, all of the contents of which are hereby incorporated by reference in their entirety. Desirably the composition is Oragene® DNA-preserving solution, Oragene® RNA-preserving solution or Genofix®. Other suitable compositions presently known or yet to be developed would be readily identified by the skilled worker.

In use, in one example, vial 500 is attached to funnel 1, and a sample from a subject is placed/delivered within chamber 2 of funnel 1. In one very specific example the sample is saliva. Processes for saliva collection are well known and will not be detailed herein. However, for subjects unable to spit (e.g., infants, young children, individuals with limitations/disabilities, animals), a sample collection tool (e.g., swab, transfer pipette) can be used for sample collection. In this case, it can be advantageous to make use of the sample expelling means within funnel 1 to obtain the sample. Similarly, a subject can be provided a liquid (e.g., mouthwash, water, saline) to gargle his/her mouth and throat or saline to flush his/her nasal cavity. Samples collected with this liquid would be delivered into the sample receiving device before or after triggering the release of the reagent substance from the reservoir in the lid.

The combination of the composition to stabilize, inactivate or disinfect or detoxify, preserve, retain viability, or facilitate the recovery of the sample component of interest can then be used in standard testing reactions, for example for detection, diagnostics, identification or quantitation. Alternatively, the combination may be stored within container system 200 and subjected to further analysis or testing at a later date. Alternatively, funnel 1 is removed from vial 500, and cap 66 is attached to the open end of vial 500. In this example, the combination can again be stored within vial 500 and subjected to further analysis or testing at a later date. In a specific example, the combination of sample and reagent is stored and later used for detection and or analysis of nucleic acid.

In one embodiment of the present invention sample receiving device 200 is appropriately sized and shaped for convenient shipping or mailing. In one example lid 100, funnel 1 and collection vial 500 of sample receiving system, are sized and shaped for shipping when funnel 1 and collection vial 500 are securely attached. Alternatively, lid 100, funnel 1 and collection vial 500 of sample receiving system, are sized and shaped for shipping when funnel 1 and collection vial 500 are separate. It will be appreciated that a variety methods of shipping are contemplated. Non-limiting examples of shipping include shipping by hand, land, air, boat, animal, and the like, or combinations thereof. Desirably, the sample receiving system of the present invention is provided in a kit format suitable for mailing in a standard mail envelope. Such a system can be sized to permit mailing via a standard European mail slot. In a specific example, the standard European mail slot has a width of about 3 cm. Alternatively, the system is sized to fit within an envelope for shipment via a standard Canadian and/or United States of America mail slot.

Another aspect of the present invention provides a method of combining a substance with a biological sample. This method comprises the steps of (i) providing a sample receiving system in accordance with the present invention, wherein the sample receiving device includes the substance; (ii) providing the biological sample; and (iii) releasing the substance from a reservoir within the lid either before or after step (ii).

Sample Receiving System Kit

Another aspect of the present invention provides a kit for collection of a sample and mixing the sample with one or more substances. The kit includes a sample receiving device in accordance with the present invention and instructions for the use thereof, with a substance stored within the reservoir in the lid of the sample receiving device and, optionally, an additional one or more reagent substances stored on a surface of the lid, funnel, sample receptacle, or a combination thereof, in such a manner that it mixes with the substance within the reservoir following its release and/or with the sample when it is introduced to the device. Such an additional reagent substance can be provided in a dried or lyophilized form that is adhered to one or more surface within the lid, funnel, sample receptacle or a combination thereof. Optionally, the sample receiving system kit includes one or more absorbent or non-absorbent sample collection tools. The collection tool can be stored within the sample receptacle prior to use. Optionally, the kit also includes a biohazard bag containing an absorbent material should the sample leak during transport.

In accordance with a specific embodiment of the present invention, the substance stored within the reservoir, alone or in combination with a second dried reagent, acts as a stabilization reagent. In one embodiment the stabilization reagent is a biomolecule stabilization reagent for stabilizing DNA, RNA and/or protein in a sample. Alternatively, the stabilization reagent functions as a storage reagent that supports the viability of a sample during transport or storage, such that infectious agents (e.g., virus, bacteria, fungus, animal cells) and/or donor cells can be cultured in the lab.

Figure 9:
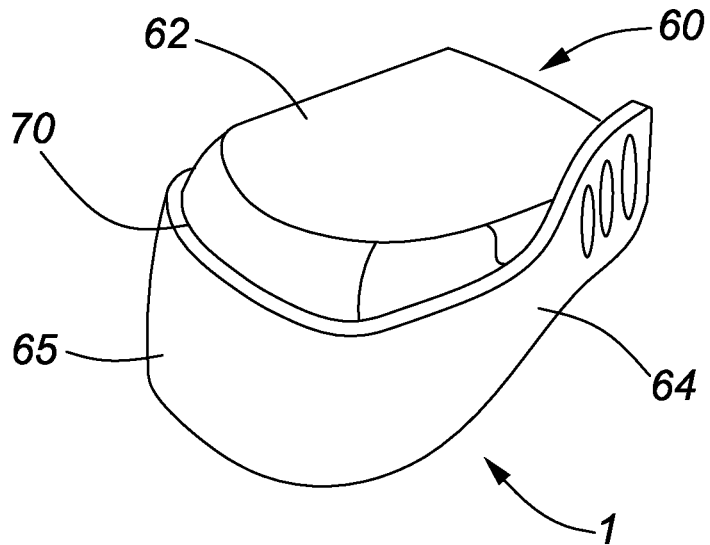
FIG. 9 is a top perspective view showing a lid guard having an alternative configuration of a tear-off strip.
Figure 10:
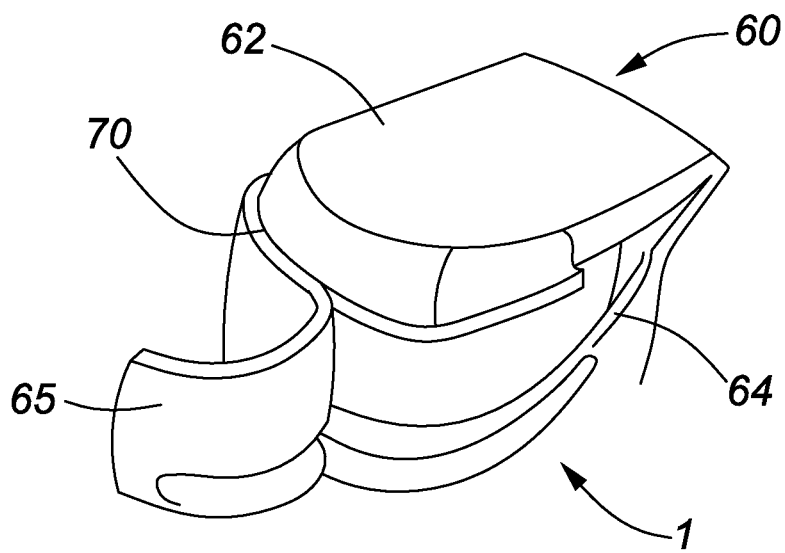
FIG. 10 is a top perspective view of the lid guard of FIG. 9 in a partially opened condition.
Figure 11A:
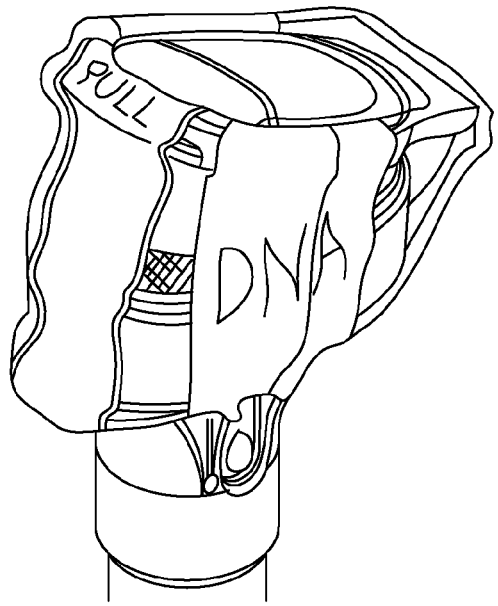
FIGS. 11A-11D depict top perspective views of four examples (A-D) of tamper detection/prevention seals on a sample receiving device in accordance with one embodiment of the present invention.
Figure 11B:
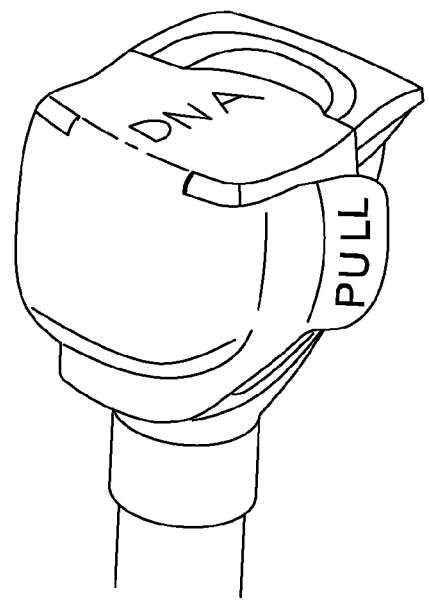
Figure 11C:
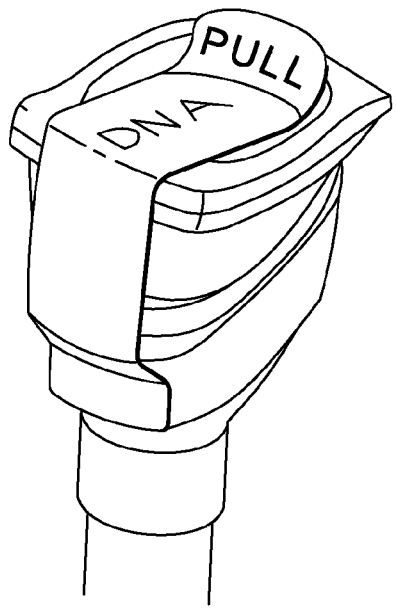
Figure 11D:
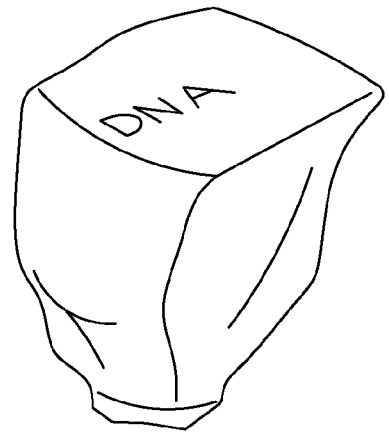
Figure 13:
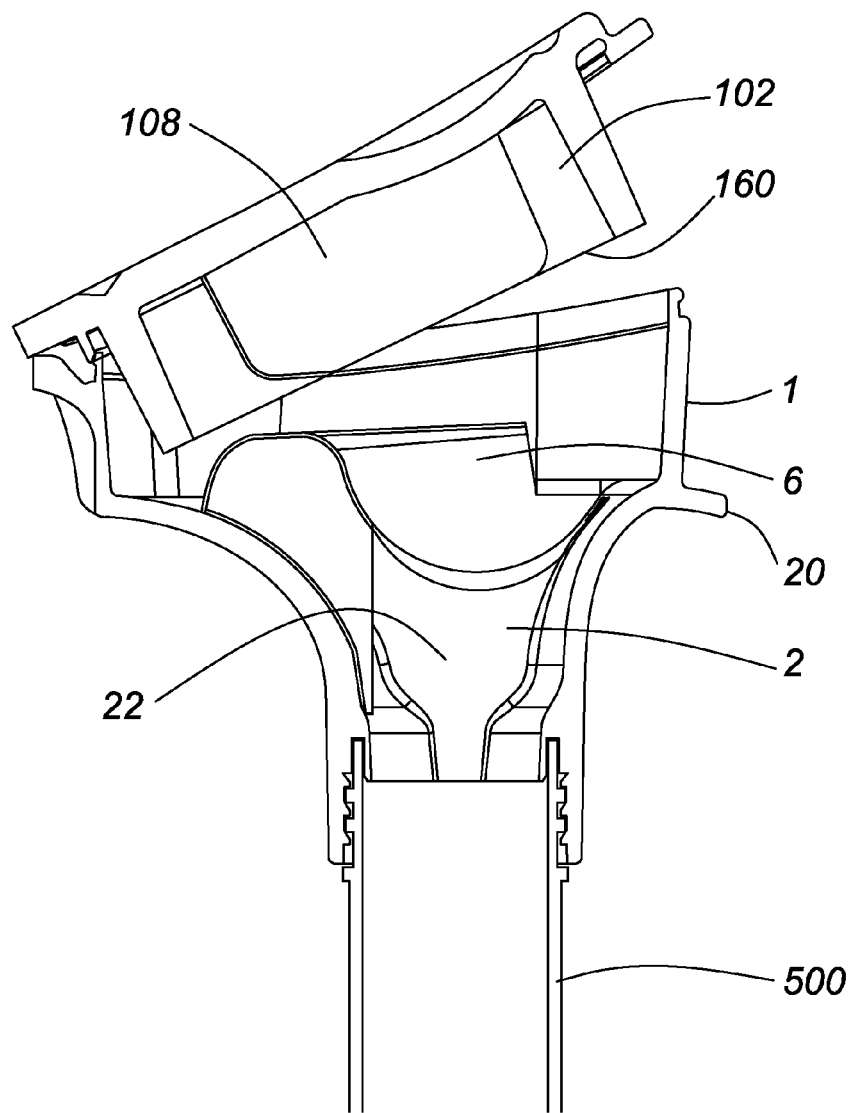
FIG. 13 is a partially transparent partial side view, depicting the sample receiving device of FIG. 1 in an initial membrane cutting position at which point the tooth is just contacting the pierceable membrane.
Figure 14:
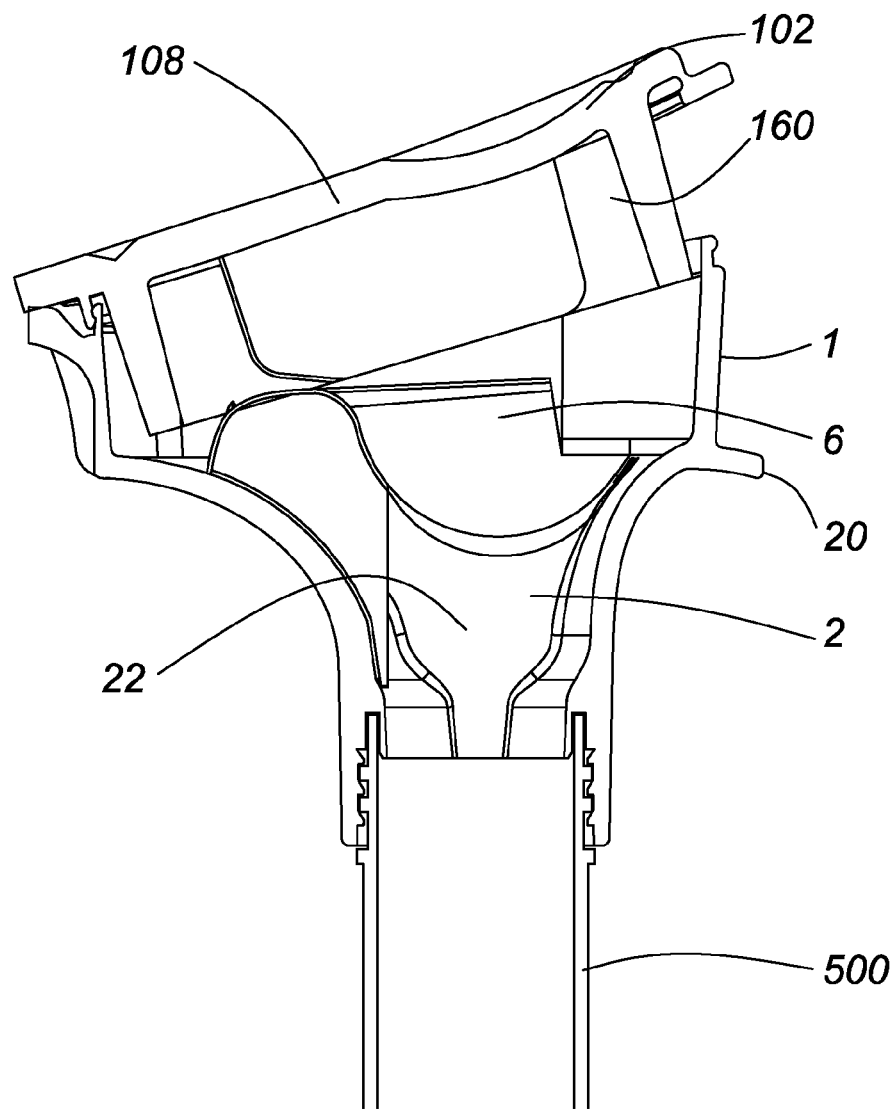
FIG. 14 is a partially transparent partial side view, depicting one embodiment of the sample receiving device of FIG. 1 in an intermediate membrane cutting position at which point the cutting rub is propagating the cut in the pierceable membrane.
Figure 15A:
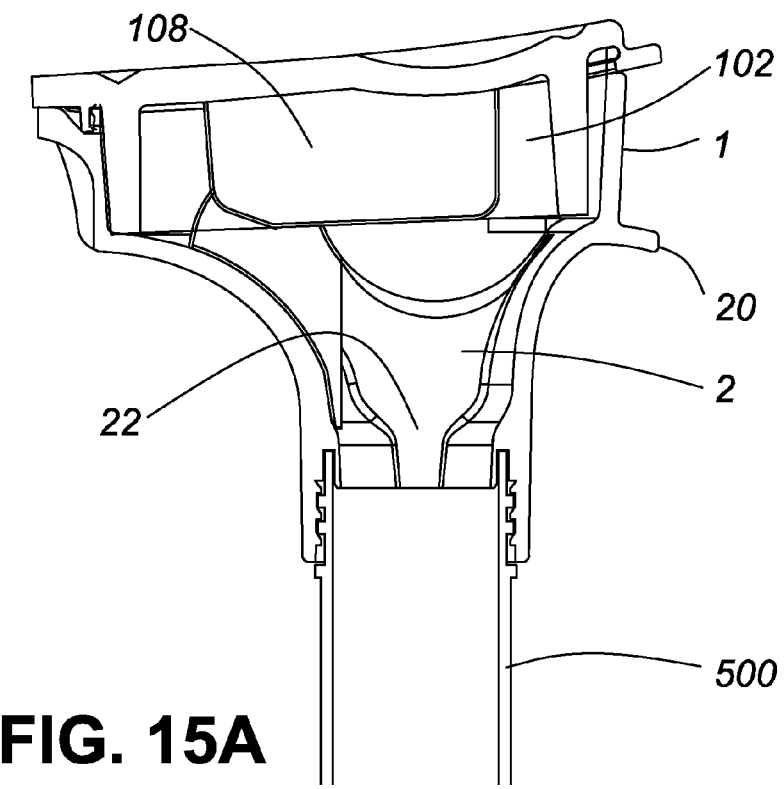
FIG. 15A is a partial side view and FIG. 15B is a partial front view, partially transparent, depicting the sample receiving device of FIGS. 1A-1B in a fully closed condition.
Figure 15B:
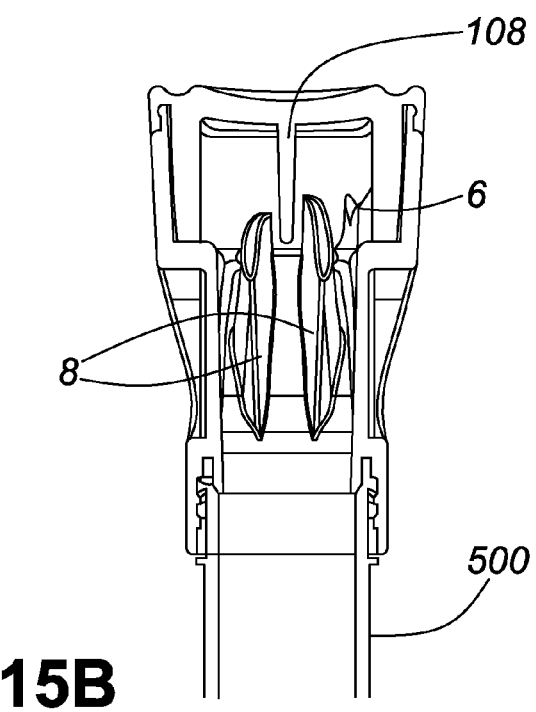
Figure 16A:
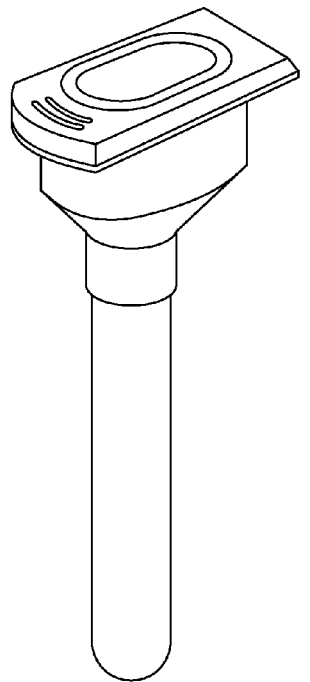
FIGS. 16A-16E depict perspective views of an alternative embodiment of the sample receiving device of the present invention in closed, partially open and fully opened conditions.
Figure 16B:
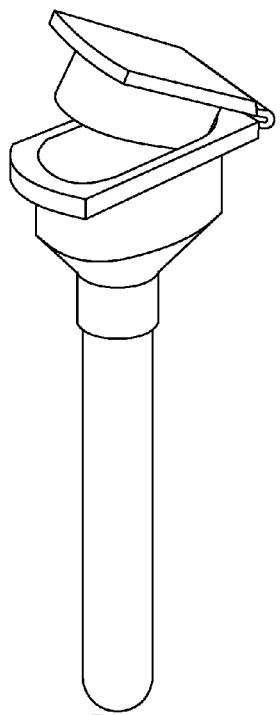
Figure 16C:
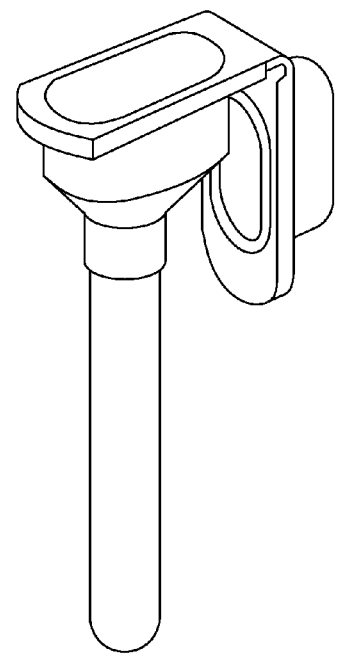
Figure 16D:
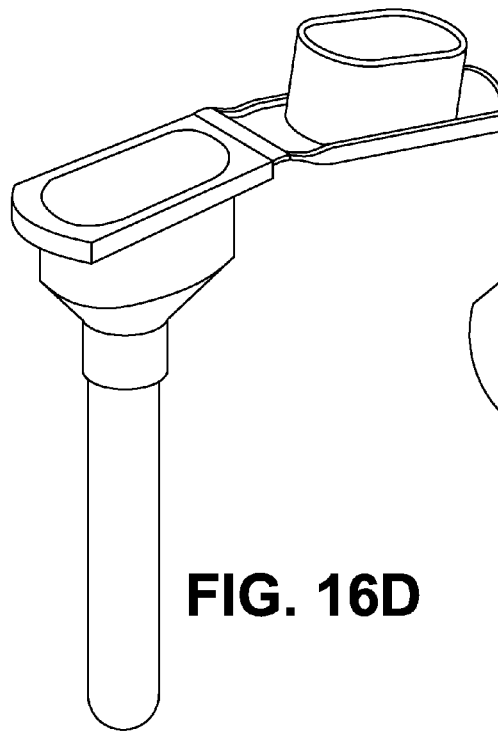
Figure 16E:
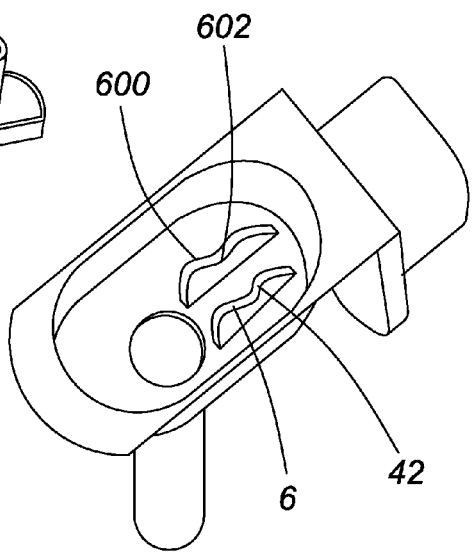
Figure 17:
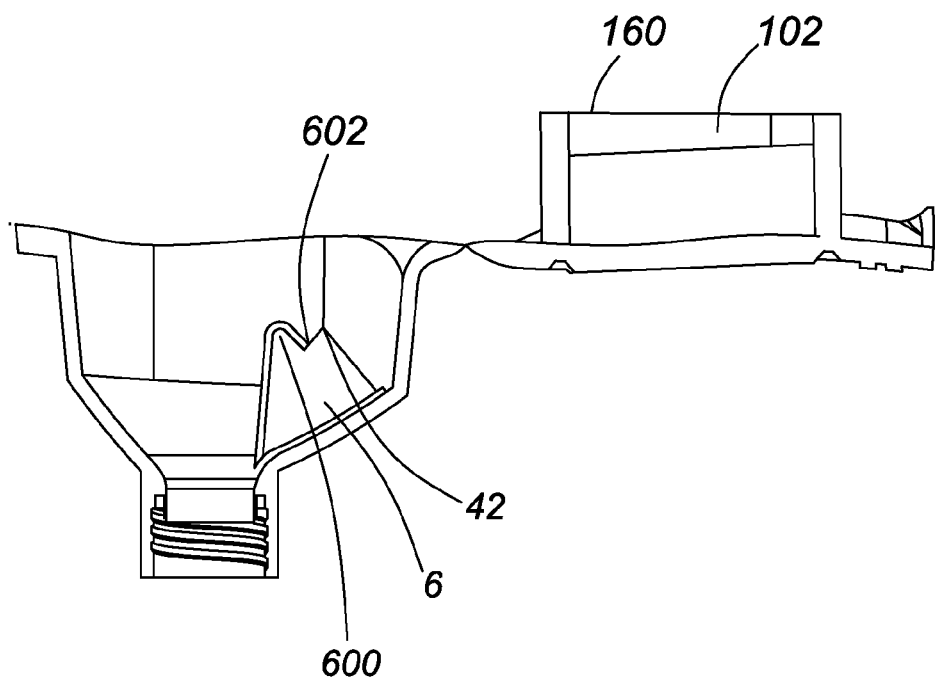
FIG. 17 is a partial side view, partially transparent, depicting the sample receiving device of FIG. 16A-16E.
Figure 29:
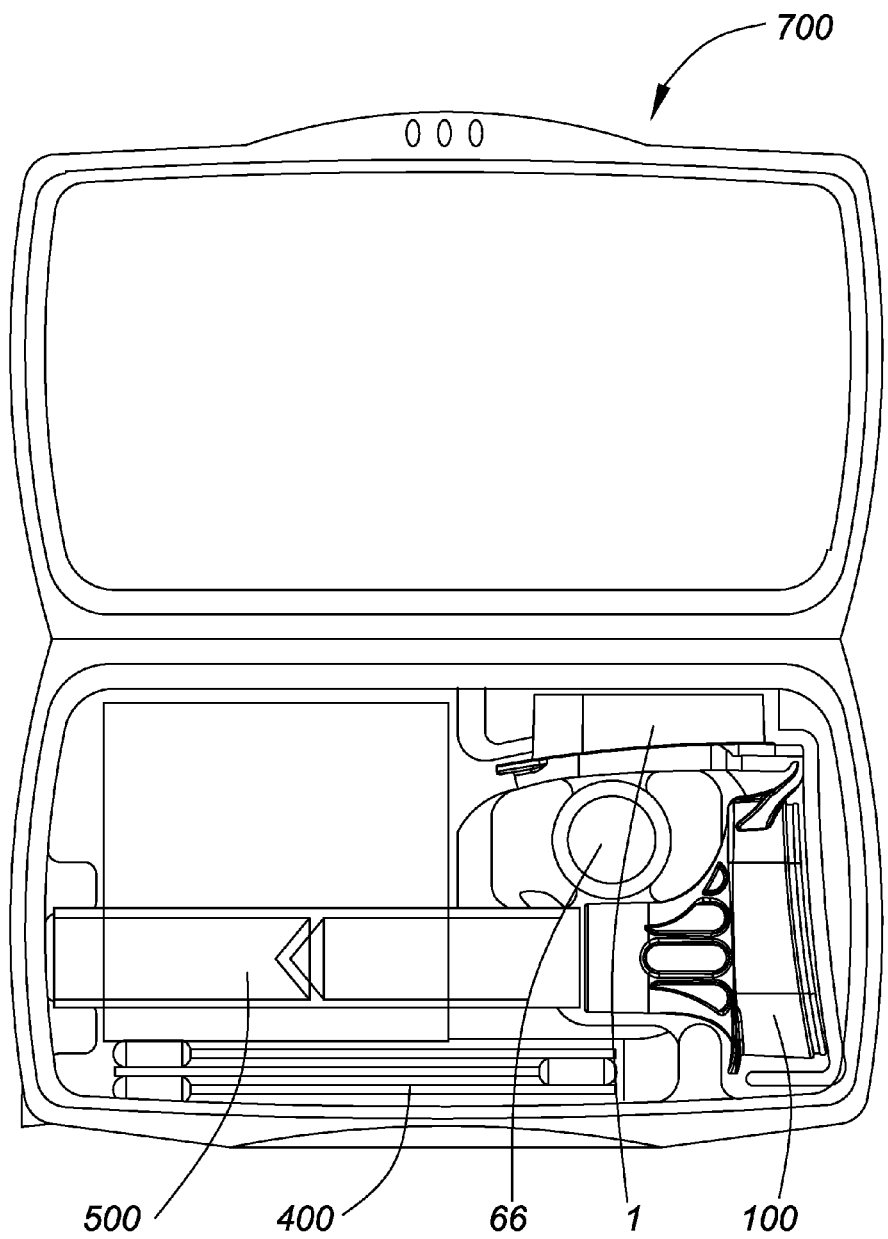
FIG. 29 is a top view of one example of packaging of a sample receiving device, in the open position.
Figure 30:
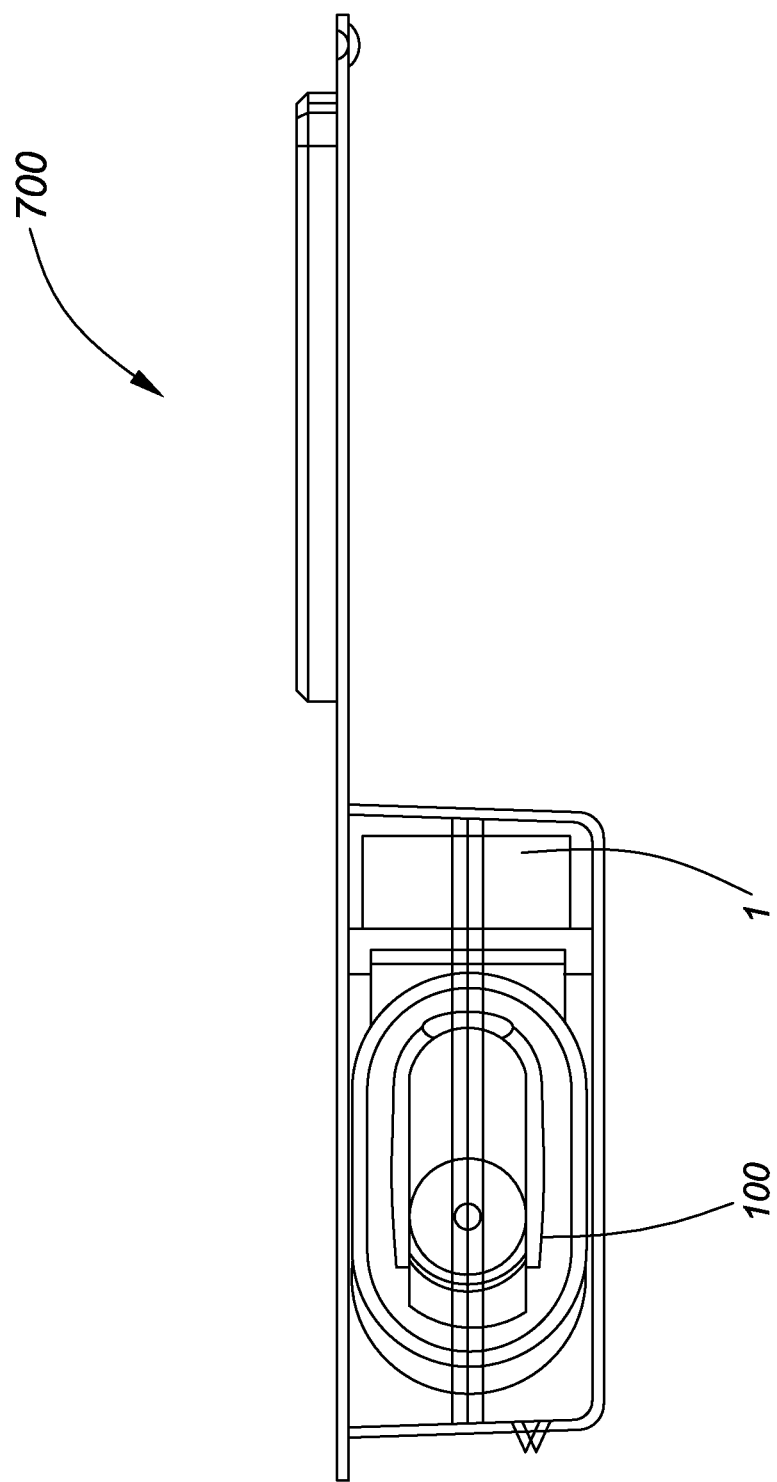
FIG. 30 is a side view of the packaging of FIG. 29, in the open position.
Figure 31A:
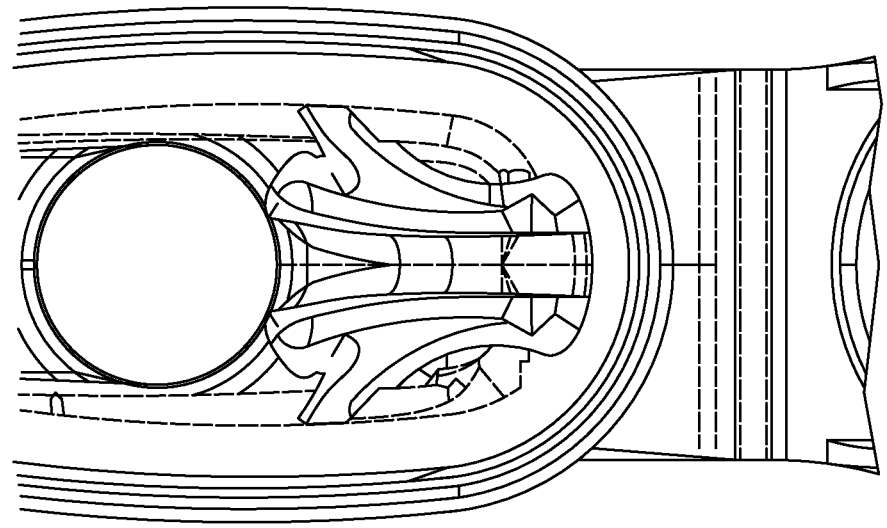
FIGS. 31A-31B depict top views of a sample receiving device in accordance with another alternative embodiment of the present invention.
Figure 31B:
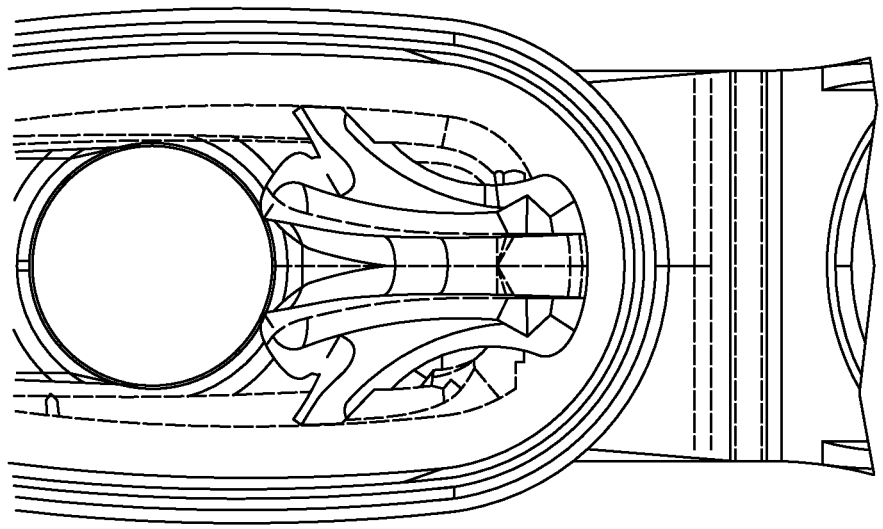
Figures 32A, 32B:
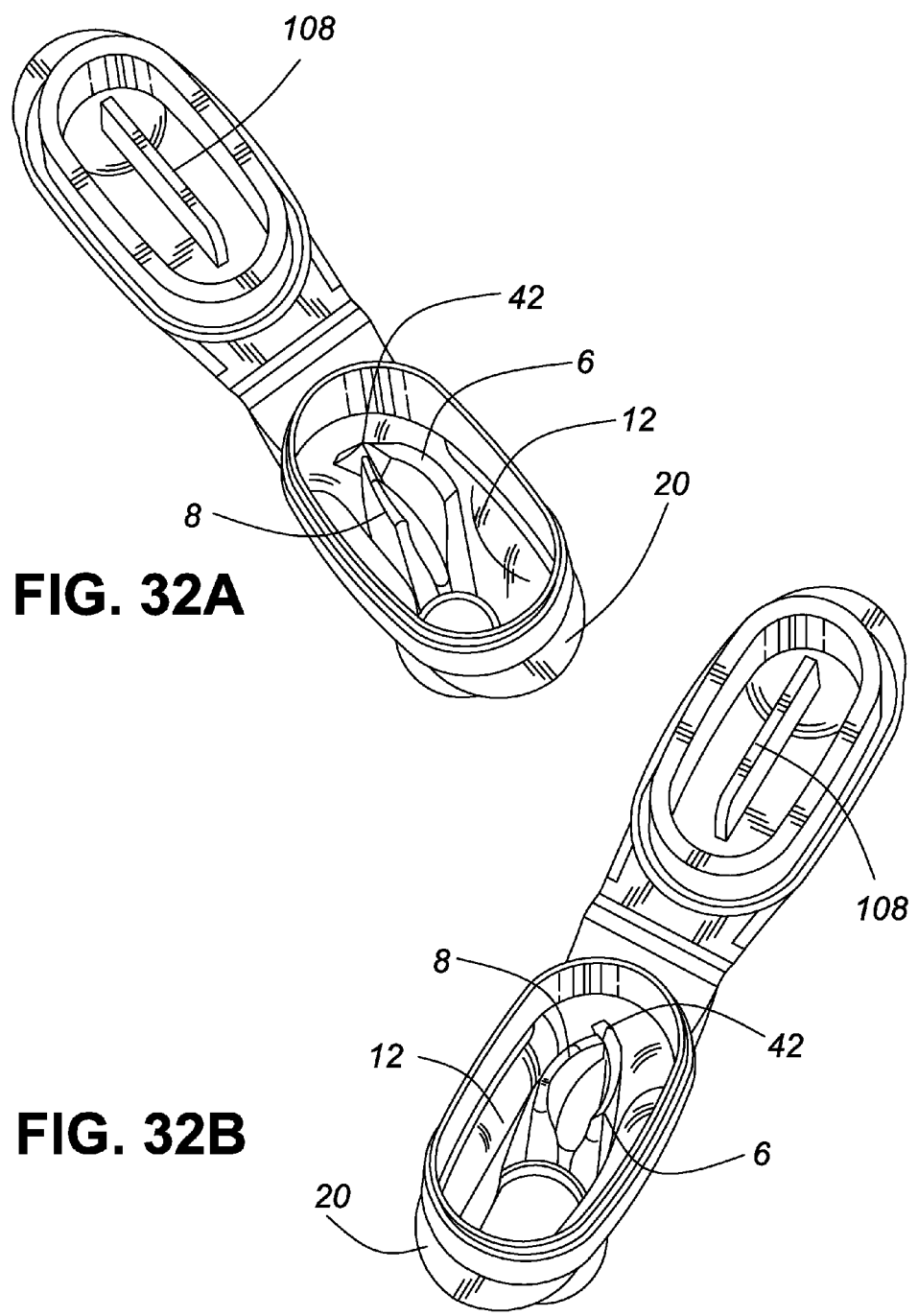
FIGS. 32A-32C depict top, left and right side perspective views and a top, front perspective view of a sample receiving device in accordance with another alternative embodiment of the present invention, which includes a unitary cutting rib.
Figure 32C:
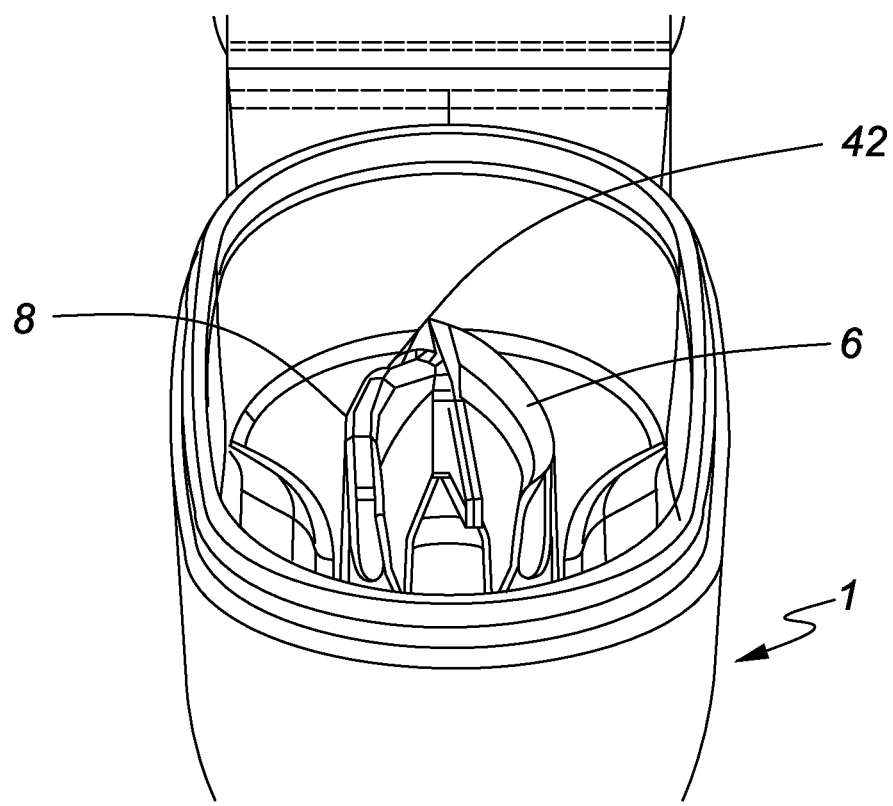
Figure 33A:
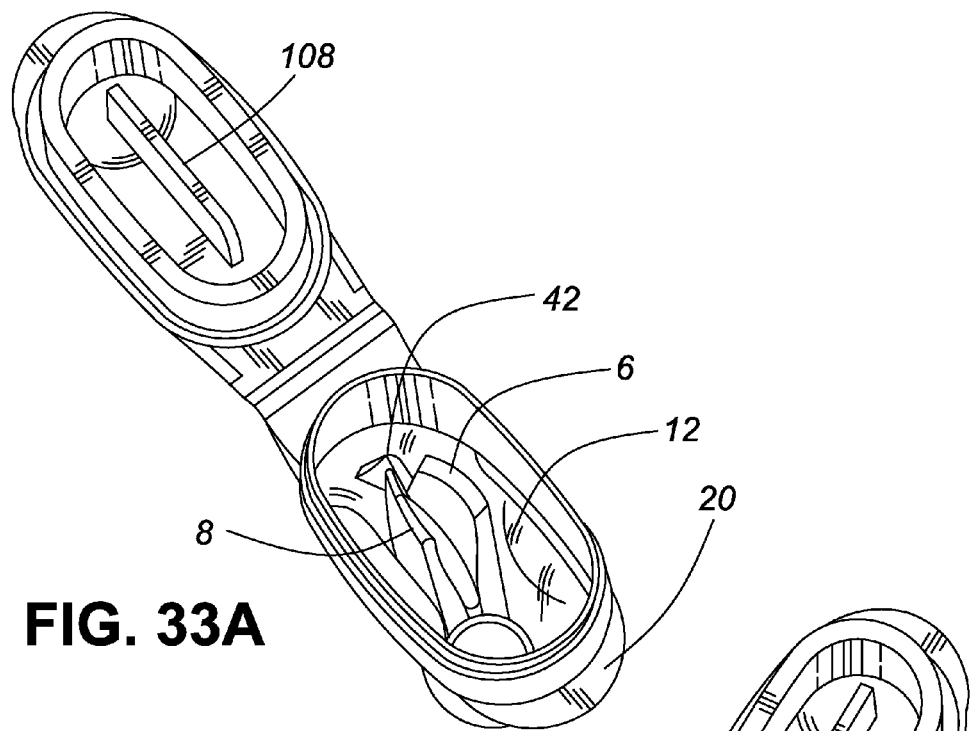
FIGS. 33A-B depict top, left and right side perspective views of a sample receiving device in accordance with another alternative embodiment of the present invention.
Figure 33B:
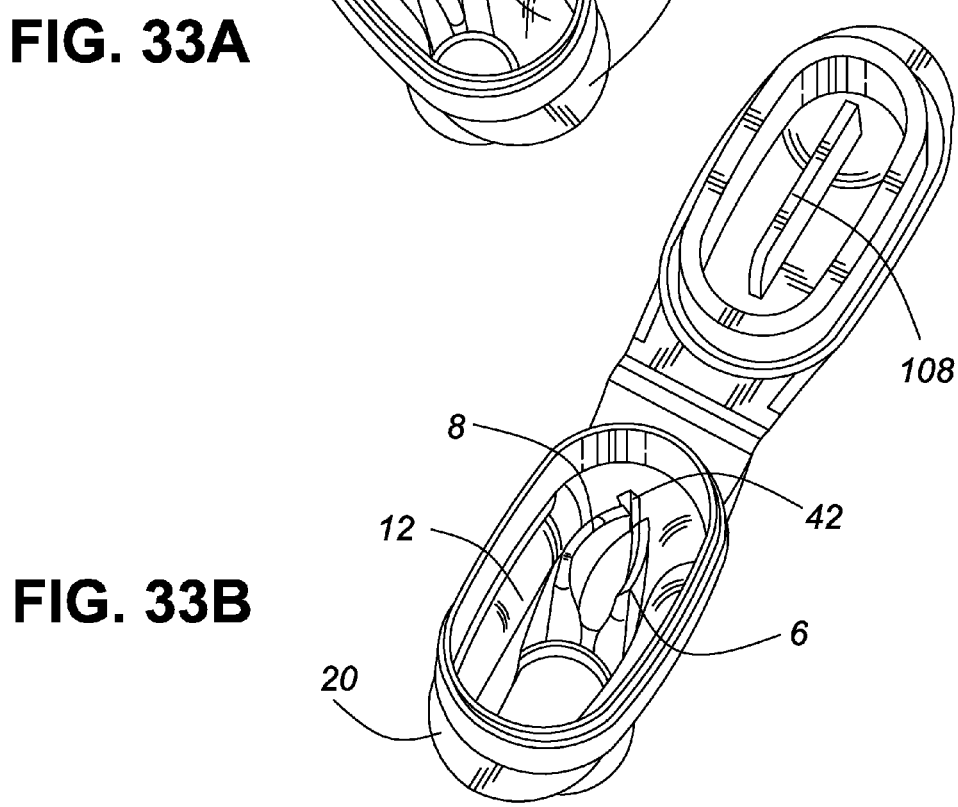

Optionally, as shown in FIGS. 29 and 30 the kit further includes packaging 700, adapted to releasably hold the sample receiving device. Such packaging is also known to the skilled worker as clamshell packaging. In the example of FIGS. 9 and 30, packaging 700 is configured to releasably hold or manage the sample receiving device with lid 190 and funnel 1 in the open position. If present, packing 700 is configured to releasably hold cap 66. Packaging 700 can be made from a variety of materials, depending on the intended use of the packaging. Packaging 700 is sized to be conveniently shipped. Packaging 700 is sized for convenient storage and/or standard shipping through the mail. Alternatively, the kit is bulk packaged with lid 100 substantially closed but locked from permitting piercing of the pierceable membrane. The lid would be managed in a safe position, for example, by housing the cap inside the funnel or placing a band of cardboard around the lid to protect the membrane.

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The embodiments of the invention in which an exclusive property or privilege is claimed are defined as follows:

1. A sample receiving device for releasably storing a composition, comprising:
   (a) a lid comprising a reservoir for retaining said composition, and a pierceable barrier sealing said composition within said reservoir; and
   b) a funnel consisting of a first open end for receiving a sample and a channel extending from said first open end to a second open end, said first open end configured for closure by said lid and for receiving said composition and said second open end being releasably or permanently attachable to a sample receptacle, wherein said funnel comprises one or more cutting ribs for cutting said pierceable barrier without a twisting action during closure of the lid, wherein the lid is attached to the funnel via a living hinge.

2. The device of claim 1, wherein said barrier is a membrane.

3. The device of claim 2, wherein said membrane is a polymeric membrane comprising two or more polymeric layers.

4. The device of claim 1, wherein the lid comprises an inner rib extending from an inner surface of the lid into the reservoir and on a plane approximately perpendicular to the plane of the barrier, wherein an outer edge of the inner rib is directly proximal to or in contact with an inner surface of the barrier.

5. The device of claim 1, wherein the lid comprises a wall defining the outer perimeter of said reservoir.

6. The device of claim 5, wherein said wall has an outer edge and said barrier is sealingly attached to said outer edge so as to cover said reservoir.

7. The device of claim 6, wherein said wall nests within the first open end of said funnel to form a fluid tight seal when the device is in a closed condition.

8. The device of claim 1, wherein the channel has an opening that is offset from the centre of said funnel and the funnel additionally includes an interior surface that is sloped downward from an interior edge toward the channel opening, and wherein said interior sloped surface defines a flow path for said composition following release of said composition from said reservoir when said barrier is cut by said one or more cutting ribs.

9. The device of claim 1, wherein said one or more cutting ribs extend upwardly toward said first open end of the funnel and each of said one or more cutting ribs comprises a sharp upper edge.

10. The device of claim 9, wherein at least one of said one or more cutting ribs comprises a piercing tooth projecting beyond said sharp upper edge.

11. The device of claim 1, which additionally comprises a tensioning means for maintaining tension on said pierceable barrier during cutting of said barrier.

12. The device of claim 1, wherein the device includes a single cutting rib.

13. The device of claim 1, wherein the device includes two cutting ribs.

14. The device of claim 13, wherein said cutting ribs are arranged opposite one another on either side of a vertical plane extending through the length of said funnel.

15. The device of claim 11, wherein said tensioning means comprises one or more tension ribs that extend upwardly toward said first open end of the funnel and each of said one or more tension ribs comprises a blunt or curved upper edge.

16. The device of claim 15, wherein each of said one or more tension ribs is rigid or resilient.

17. The device of claim 15 which comprises a single cutting rib having a piercing tooth and a single tension rib, wherein said cutting rib and tension rib are arranged in a curved "V" shape forming a pocket region such that the piercing tooth is at the apex of the "V", and wherein the wide end of the "V" is adjacent the opening of the channel.

18. The device of claim 17, wherein the cutting rib extends further toward the first open end of said funnel than the tensioning rib.

19. The device of claim 1, wherein the funnel additionally comprises an expelling means for expelling the sample from a sample-containing absorbent device into the channel of said funnel.

20. The device of claim 1, wherein the reservoir is sized to accommodate about 0.1 ml to about 10.0 ml of said first substance.

21. The device of claim 1, which additionally comprises a removable lid guard.

22. A sample receiving device for releasably storing a composition, comprising:
   (a) a lid comprising:
      (i) a wall defining an outer perimeter of a reservoir for retaining said composition;
      (ii) a pierceable barrier sealingly attached to an outer edge of said wall so as to seal said composition within said reservoir; and
      (iii) an inner rib extending from an inner surface of the lid into the reservoir and on a plane approximately perpendicular to the plane of the barrier, wherein an outer edge of the inner rib is directly proximal to or in contact with an inner surface of the barrier; and
   b) a funnel having a first open end for receiving a sample and configured for closure by said lid, and a second open end for releasable or permanent attachment to a sample receptacle, wherein the lid is attached to the funnel via a living hinge, and wherein said funnel comprises:
      (i) a channel extending from said first open end to said second open end;
      (ii) one or more cutting ribs for cutting said pierceable barrier without a twisting action during closure of the lid, each of said cutting ribs having a sharp upper edge, wherein at least one of said one or more cutting ribs comprises a piercing tooth projecting beyond said sharp upper edge; and (iii) one or more tension ribs that extend upwardly toward said first open end of the funnel, wherein each of said one or more tension ribs comprises a blunt or curved upper edge.

23. A sample collection kit comprising a sample receiving device according to claim 1, wherein the kit additionally includes said composition, and wherein said composition is a stabilization reagent.

24. The sample collection kit of claim 23, wherein the stabilization reagent is a biomolecule stabilization reagent.

25. The sample collection kit of claim 24, wherein said kit additionally comprises a sample collection tube for attachment to said second open end of funnel.

26. The sample collection kit of claim 25, wherein said sample collection tube attaches to said second open end of said funnel via a screw thread.

27. The sample collection kit of claim 23, wherein the kit additionally comprises an additional one or more reagent substances stored in a dried or lyophilized form adhered to one or more inner surfaces of said lid, funnel or sample collection tube.

28. The sample collection kit of claim 23 wherein the kit additionally comprises one or more absorbent or non-absorbent sample collection tools.

29. A sample receiving device for releasably storing a composition, comprising:
  (a) a lid comprising a reservoir for retaining said composition, and a pierceable barrier sealing said composition within said reservoir; and
  b) a funnel consisting of:
    i) a first open end for receiving a sample and a channel extending from said first open end to a second open end, said first open end configured for closure by said lid and for receiving said composition and said second open end being releasably or permanently attachable to a sample receptacle; and
    ii) one or more cutting ribs for cutting said pierceable barrier without a twisting action during closure of the lid, wherein the lid is attached to the funnel via a living hinge.

30. A sample receiving device for releasably storing a composition, comprising:
  (a) a lid comprising:
    (i) a wall defining an outer perimeter of a reservoir for retaining said composition;
    (ii) a pierceable barrier sealingly attached to an outer edge of said wall so as to seal said composition within said reservoir; and
    (iii) an inner rib extending from an inner surface of the lid into the reservoir and on a plane approximately perpendicular to the plane of the barrier, wherein an outer edge of the inner rib is directly proximal to or in contact with an inner surface of the barrier; and
  (b) a funnel consisting of:
    (i) a first open end for receiving a sample and configured for closure by said lid, and a second open end for releasable or permanent attachment to a sample receptacle;
    (ii) a channel extending from said first open end to said second open end;
    (iii) one or more cutting ribs for cutting said pierceable barrier without a twisting action during closure of the lid, each of said cutting ribs having a sharp upper edge, wherein at least one of said one or more cutting ribs comprises a piercing tooth projecting beyond said sharp upper edge; and
    (iv) one or more tension ribs that extend upwardly toward said first open end of the funnel, wherein each of said one or more tension ribs comprises a blunt or curved upper edge, wherein the lid is attached to the funnel via a living hinge.

* * * * *